US007902227B2

(12) United States Patent
Macielag et al.

(10) Patent No.: US 7,902,227 B2
(45) Date of Patent: Mar. 8, 2011

(54) C-7 ISOXAZOLINYL QUINOLONE / NAPHTHYRIDINE DERIVATIVES USEFUL AS ANTIBACTERIAL AGENTS

(75) Inventors: Mark J. Macielag, Branchburg, NJ (US); Michele A. Weidner-Wells, Hillsborough, NJ (US); Shu-Chen Lin, High Bridge, NJ (US)

(73) Assignee: Janssen Pharmaceutica NV., Beerse (BE)

( * ) Notice: Subject to any disclaimer, the term of this patent is extended or adjusted under 35 U.S.C. 154(b) by 0 days.

(21) Appl. No.: 12/180,641

(22) Filed: Jul. 28, 2008

(65) Prior Publication Data

US 2009/0029980 A1   Jan. 29, 2009

(51) Int. Cl.
*C07D 215/00* (2006.01)
*A01N 43/42* (2006.01)
*A61K 31/47* (2006.01)
(52) U.S. Cl. ......................................... 514/312; 546/156
(58) Field of Classification Search .................. 546/156; 514/312
See application file for complete search history.

(56) References Cited

U.S. PATENT DOCUMENTS

| 4,777,253 | A | 10/1988 | Mitscher et al. |
| 4,822,801 | A | 4/1989 | Domagala et al. |
| 4,894,458 | A | 1/1990 | Masuzawa et al. |
| 4,990,517 | A | * 2/1991 | Petersen et al. ............... 514/300 |
| 5,017,581 | A | 5/1991 | Nishitani et al. |
| 5,077,429 | A | 12/1991 | Grohe et al. |
| 5,256,662 | A | 10/1993 | Domagala et al. |
| 5,677,456 | A | 10/1997 | Kim et al. |
| 5,688,791 | A | 11/1997 | Kimura et al. |
| 5,822,801 | A | 10/1998 | Varney |
| 5,869,670 | A | 2/1999 | Hong et al. |
| 5,880,283 | A | 3/1999 | Matsumoto et al. |
| 6,025,370 | A | 2/2000 | Todu et al. |
| 6,156,903 | A | 12/2000 | Yazaki et al. |
| 6,329,391 | B1 | 12/2001 | Ledoussal et al. |
| 6,573,260 | B1 | 6/2003 | Takemura et al. |
| 7,189,847 | B2 | 3/2007 | Sato et al. |
| 2002/0049192 | A1 | 4/2002 | Ledoussal |
| 2002/0049223 | A1 | 4/2002 | Elmore et al. |

FOREIGN PATENT DOCUMENTS

| DE | 3142854 A1 | * 10/1981 |
| EP | 023095 B1 | * 1/1981 |
| EP | 047005 B1 | * 3/1982 |
| EP | 195316 A1 | * 9/1986 |
| EP | 230053 A2 | * 12/1986 |
| EP | 304087 B1 | * 2/1989 |
| EP | 191451 B1 | * 8/1989 |
| EP | 342849 A2 | * 11/1989 |
| EP | 343524 A1 | * 11/1989 |
| EP | 153163 B1 | * 12/1989 |
| EP | 362759 A1 | * 11/1990 |
| EP | 153828 B1 | * 12/1990 |
| EP | 413455 B1 | * 2/1991 |
| EP | 421668 B1 | * 10/1991 |
| EP | 487030 A2 | * 5/1992 |
| EP | 572259 A1 | * 12/1993 |
| EP | 677522 A1 | * 10/1995 |
| EP | 688772 B1 | * 12/1995 |
| EP | 976749 A1 | * 2/2000 |
| EP | 1031569 A1 | * 8/2000 |
| JP | 48-472 | * 9/1973 |
| JP | 64-90184 A | * 4/1989 |
| JP | 6-70456 | * 3/1994 |
| JP | 6-73056 A | * 3/1994 |
| JP | 6-263754 | * 9/1994 |
| JP | 10-130241 A | * 5/1998 |
| WO | WO 92/09579 A1 | 11/1992 |
| WO | WO 92/22550 A1 | 12/1992 |
| WO | WO 94/07873 A1 | 4/1994 |
| WO | WO 94/15933 A1 | 7/1994 |
| WO | WO 96/19472 A1 | 6/1996 |
| WO | WO 97/11068 A1 | 3/1997 |
| WO | WO 97/29102 A1 | 8/1997 |
| WO | WO 99/14214 A1 | 3/1999 |
| WO | WO 00/31062 A1 | 2/2000 |
| WO | WO 00/49192 A1 | 8/2000 |
| WO | WO 00/71541 A1 | 11/2000 |
| WO | WO 01/18005 A1 | 3/2001 |
| WO | WO 01/36408 A1 | 5/2001 |
| WO | WO 01/85728 A2 | 11/2001 |
| WO | WO 02/09758 A2 | 2/2002 |
| WO | WO 02/48138 A1 | 6/2002 |
| WO | WO 02/085886 A2 | 10/2002 |
| WO | WO 03/011450 A1 | 2/2003 |
| WO | WO 03/014108 A1 | 2/2003 |
| WO | WO 03/028665 A2 | 4/2003 |
| WO | WO 03/050107 A1 | 6/2003 |

OTHER PUBLICATIONS

Mitten et al., Antimicrobial agents and chemotherapy, (Sep. 2001) vol. 45, No. 9, pp. 2585-2593.*
Albrecht, R. "Development of Antibacterial Agents of the Nalidixic Acid Type", Antibacterial Agents, vol. 21 (1977) pp. 9-104.
Cornett, J. B., et al. "Chapter 14, Quinolone Antibacterial Agents", Annual Reports in Medicinal Chemistry, vol. 21 (1986) pp. 139-148.
Domagala, J. M., et al. "1-Substituted 7-[3-[(Ethylamino)methyl]-1-pyrrolidinyl]- 6,8-difluoro-1,4-dihydro-4-oxo-3-quinolinecarboxylic acids. New quantitative Structure-Activity Relationships at $N_1$ for the Quinolone Antibacterials", J. Medicinal Chemistry (1988) vol. 31, pp. 991-1001.
Fernandes, P., et al. "Section III—Chemotherpeutic Agents, Chapter 12, quinolones", Annual Rpeorts in Medicinal Chemistry, vol. 22 (1987) pp. 117-126.
Klopman, G., et al. "Computer Automated Structure Evaluation of Quinolone Antiabacterial Agents", Antimicrobial Agents and Chemotherapy, (1987), vol. 31, No. 11, pp. 1831-1840.
Koga, H., et al. "Structure-Activity Relationships of Antibacterial 6,7- and 7,8- Disubstituted 1-Alkyl-1,4-dihydro-4-oxoquinolone-3-carboxylic Acids", J. Medical Chemistry (1980) vol. 23, pp. 1358-1363.

(Continued)

*Primary Examiner* — D. Margaret Seaman
*Assistant Examiner* — Niloofar Rahmani
(74) *Attorney, Agent, or Firm* — Thomas Dodd

(57) ABSTRACT

The present invention relates to C-7 isoxazolyl quinoline/naphthyridine derivatives useful as antimicrobial compounds, pharmaceutical compositions comprising said derivatives and the use of said derivatives and pharmaceutical compositions as antimicrobial agents against pathogenic microorganisms, particularly against resistant microbes.

10 Claims, No Drawings

OTHER PUBLICATIONS

Kuramoto, Y., et al. "A Novel Antibacterial 8-Chloroquinolone with a Distorted Orientation of the N1-(5-Amino-2,4-difluorophenyl) Group", J. Medical Chemistry (2003) vol. 46, pp. 1905-1917.

Ledoussal, B., et al. "Potent Non-6-Fluoro-Substiturted Quinolone Antibacterials: Synthesis and Biological Activity", J. Medical Chemistry (1992) vol. 35, pp. 198-200.

Rosen, T., et al. "Design, Synthesis, and Properties of (4S)-7-(4-Amino-2-substituted-pyrrolidin-1-yl)quinolone-3-carboxylic Acids", J. Medicinal Chemistry (1988) vol. 31,pp. 1958-1611.

Ruiz, J. "Mechanisms of Resistance to Quinolones; Target Alterations, Decreased Accumulation and DNA Gyrase Protection", Journal of Antimicrobial Chemotherapy (2003) vol. 51, pp. 1109-1117.

Sanders, W., et al. "Inducible β-Lactamases: Clinical and Epidemiologic Implications for Use of Newer Cephalosporins", Review of Infectious Diseases, vol. 10, No. 4 (1988) pp. 830-838.

Wentland, M., et al. "Chapter 15. Quinolone Antibacterial Agents", Annual Reports in Medicinal Chemistry.

Wolfson, J., et al. "The Fluoroquinolones; Structures, Mechanisms of Action and Resistance, and Specra of Activity in Vitro", Antimicrobial Agents and Chemotherapy(1985) vol. 28, No. 4 pp. 581-586.

Ziegler, C., et al. "Synthesis of Some Novel 7-Substituted Quinolonecarboxylic Acids *via* Nitroso and Nitrone Cycloadditions", J. Heterocyclic Chemistry, vol. 25 (1988) pp. 719-723.

* cited by examiner

C-7 ISOXAZOLINYL QUINOLONE / NAPHTHYRIDINE DERIVATIVES USEFUL AS ANTIBACTERIAL AGENTS

FIELD OF THE INVENTION

The present invention relates to C-7 isoxazolyl quinoline/naphthyridine derivatives useful as antimicrobial compounds, pharmaceutical compositions comprising said derivatives and the use of said derivatives and pharmaceutical compositions as antimicrobial agents against pathogenic microorganisms, particularly against resistant microbes.

BACKGROUND OF THE INVENTION

The chemical and medical literature describes compounds that are said to be antimicrobial, i.e., capable of destroying or suppressing the growth or reproduction of microorganisms, such as bacteria. For example, such antibacterial agents are described in Antibiotics, Chemotherapeutics, and Antibacterial Agents for Disease Control (M. Greyson, editor, 1982), E. Gale et al., The Molecular Basis of Antibiotic Action 2d edition (1981), Recent Research Developments in Antimicrobial Agents & Chemotherapy (S. G. Pandalai, Editor, 2001), Quinolone Antimicrobial Agents (John S Wolfson, David C Hooper, Editors, 1989), and F. O'Grady, H. P. Lambert, R. G. Finch, D. Greenwood, Martin Dedicoat, "Antibiotic and Chemotherapy, 7th edn." (1997).

The mechanisms of action of these antibacterial agents vary. However, they are generally believed to function in one or more ways: by inhibiting cell wall synthesis or repair; by altering cell wall permeability; by inhibiting protein synthesis; or by inhibiting the synthesis of nucleic acids. For example, beta-lactam antibacterial agents act through inhibiting essential penicillin binding proteins (PBPs) in bacteria, which are responsible for cell wall synthesis. As another example, quinolones act, at least in part by inhibiting synthesis of DNA, thus preventing the cell from replicating.

The pharmacological characteristics of antimicrobial agents, and their suitability for any given clinical use, vary. For example, the classes of antimicrobial agents (and members within a class) may vary in 1) their relative efficacy against different types of microorganisms, 2) their susceptibility to development of microbial resistance and 3) their pharmacological characteristics such as their bioavailability and biodistribution. Accordingly, selection of an appropriate antimicrobial agent in a given clinical situation requires analysis of many factors, including the type of organism involved, the desired method of administration, the location of the infection to be treated and other considerations.

However, many such attempts to produce improved antimicrobial agents yield equivocal results. Indeed, few antimicrobial agents are produced that are truly clinically acceptable in terms of their spectrum of antimicrobial activity, avoidance of microbial resistance, and pharmacology. Thus there is a continuing need for broad-spectrum antimicrobial agents, which are effective against resistant microbes.

Examples of bacterial infections resistant to antibiotic therapy have been reported in the past; they are now a significant threat to public health in the developed world. The development of microbial resistance (perhaps as a result of the intense use of antibacterial agents over extended periods of time) is of increasing concern in medical science. "Resistance" can be defined as existence of organisms, within a population of a given microbial species, that are less susceptible to the action of a given antimicrobial agent. This resistance is of particular concern in environments such as hospitals and nursing homes, where relatively high rates of infection and intense use of antibacterial agents are common. See, e.g., W. Sanders, Jr. et al., "Inducible Beta-lactamases: Clinical and Epidemiologic Implications for the Use of Newer Cephalosporins", *Review of Infectious Diseases*, p. 830 (1988).

Pathogenic bacteria are known to acquire resistance via several distinct mechanisms including inactivation of the antibiotic by bacterial enzymes (e.g., β-lactamases hydrolyzing penicillin and cephalosporins); removal of the antibiotic using efflux pumps; modification of the target of the antibiotic via mutation and genetic recombination (e.g., penicillin-resistance in *Neiserria gonorrhea*); and acquisition of a readily transferable gene from an external source to create a resistant target (e.g., methicillin-resistance in *Staphylococcus aureus*). There are certain Gram-positive pathogens, such as vancomycin-resistant *Enterococcus faecium*, which are resistant to most commercially available antibiotics.

Hence existing antibacterial agents have limited capacity in overcoming the threat of resistance. Thus it would be advantageous to provide new antibacterial agents that can be used against resistant microbes.

Some 1,4-dihydroquinolone, naphthyridine or related heterocyclic moieties are known in the art to have antimicrobial activity and are described in the following references: R. Albrecht Prog. Drug Research, Vol. 21, p. 9 (1977); J. Wolfson et al., "The Fluoroquinolones: Structures, Mechanisms of Action and Resistance, and Spectra of Activity In Vitro", Antimicrob. Agents and Chemother., Vol. 28, p. 581 (1985); G. Klopman et al. Antimicrob. Agents and Chemother., Vol. 31, p. 1831 (1987); M. P. Wentland et al., Ann. Rep. Med. Chem., Vol. 20, p. 145 (1986); J. B. Cornett et al., Ann. Rep. Med. Chem., Vol. 21, p. 139 (1986); P. B. Fernandes et al. Ann. Rep. Med. Chem., Vol. 22, p. 117 (1987); A. Koga, et al. "Structure-Activity Relationships of Antibacterial 6,7- and 7,8-Disubstituted 1-alkyl-1,4-dihydro-4-oxoquinoline-3-carboxylic Acids" J. Med. Chem. Vol. 23, pp. 1358-1363 (1980); J. M. Domagala et al., J. Med. Chem. Vol. 31, p. 991 (1988); T. Rosen et al., J. Med. Chem. Vol. 31, p. 1598 (1988); B. Ledoussal et al., "Non 6-Fluoro Substituted Quinolone Antibacterials: Structure and Activity", J. Med. Chem. Vol. 35, p. 198-200 (1992); U.S. Pat. No. 6,329,391; A. M Emmerson et al., "The quinolones: Decades of development and use", J. Antimicrob. Chemother., Vol 51, pp 13-20 (2003); J. Ruiz, "Mechanisms of resistance to quinolones: target alterations, decreased accumulation and DNA gyrase protection" J. Antimicrob. Chemother. Vol. 51, pp 1109-1117 (2003); Y. Kuramoto et al., "A Novel Antibacterial 8-Chloroquinolone with a Distorted Orientation of the N1-(5-Amino-2,4-difluorophenyl) Group" J. Med. Chem. Vol. 46, pp 1905-1917 (2003); Japanese Patent Publication 06263754; European Patent Publication 487030; International Patent Publication WO0248138; International Patent Publication WO9914214; U.S. Patent Publication 2002/0049192; International Patent Publication WO02085886; European Patent Publication 572259; International Patent Publication WO0136408; U.S. Pat. No. 5,677,456; European Patent Publication 362759; U.S. Pat. No. 5,688,791; U.S. Pat. No. 4,894,458; European Patent Publication 677522; U.S. Pat. No. 4,822,801; U.S. Pat. No. 5,256,662; U.S. Pat. No. 5,017,581; European Patent Publication 304087; International Patent Publication WO0136408; International Patent Publication WO02085886; Japanese Patent Publication 01090184; International Patent Publication WO9209579; International Patent Publication WO0185728; European Patent Publication 343524; Japanese Patent Publication 10130241; European Patent Publication 413455; International Patent Publication WO0209758; International Patent Publication WO0350107; International Patent Publication WO9415933; International Patent Publication WO9222550; Japanese Patent Publication 07300472; International Patent Publication WO0314108; International Patent Publication WO0071541; International Patent Publication WO0031062; and U.S. Pat. No. 5,869,670.

U.S. Pat. No. 4,990,517 discloses quinolone and naphthyridine antibacterial agents of the formula,

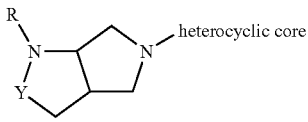

wherein Y is O, $CH_2$, $CH_2CH_2$, or $CH_2O$, R is hydrogen, optionally hydroxyl-substituted $C_1$-$C_4$-alkyl, as well as phenyl, benzyl, $C_1$-$C_4$-alkoxycarbonyl, $C_1$-$C_4$-acyl, (5-methyl-2-oxo-1,3-dioxol-4-yl)methyl, or $C_3$-$C_8$-cycloalkyl, and the heterocyclic core is a 3-quinolone- or naphthyridone carboxylic acid derivative.

The synthesis of a compound of the formula,

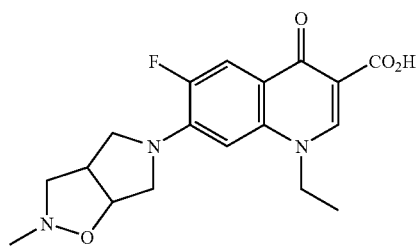

is disclosed in the Journal of Heterocyclic Chemistry, 1988, 25, 719-723.

Japanese patent 06073056A describes antibacterial 3-quinolone-carboxylic acid and 1,8-naphthyridinecarboxylic acid derivatives of the formula,

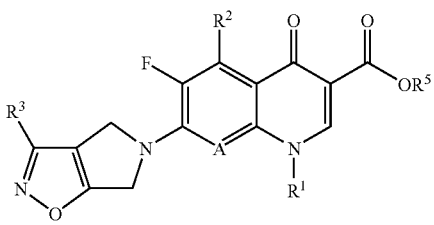

wherein $R^1$ is (un)substituted $C_1$-$C_6$-alkyl, $C_2$-$C_6$-alkenyl, $C_3$-$C_7$-cycloalkyl, or aryl, $R^2$ is hydrogen, halogen, (un)protected OH, $NH_2$, $C_1$-$C_6$ alkylamino, or di($C_1$-$C_6$-alkyl)amino, $R_3$ and $R_5$ are hydrogen or $C_1$-$C_6$-alkyl, and A is N or $CA^1$, wherein $A^1$ is hydrogen, halogen, $C_1$-$C_6$-alkyl, (un)substituted $C_1$-$C_6$-alkoxy, cyano, nitro, or $A^1$ together with $R^1$ may form a ring optionally containing O, N, or S or substituted by $C_1$-$C_6$-alkyl.

SUMMARY OF THE INVENTION

Applicants have found a novel series of C-7 isoxazolinyl quinolone/naphthyridine derivatives that are effective against resistant microbes, and provide significant activity advantages over the art. In particular, the invention relates to compounds having a structure according to Formula (I)

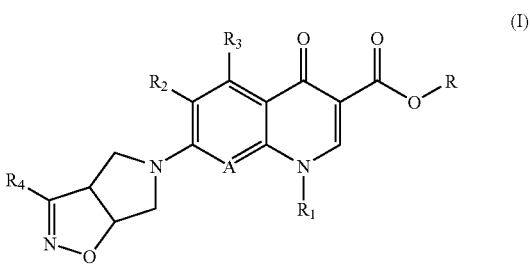

wherein

R is selected from the group consisting of hydrogen and lower alkyl;

$R_1$ is selected from the group consisting of $C_3$-$C_6$cycloalkyl, $C_4$-$C_6$heterocycloalkyl, $C_1$-$C_8$alkyl, $C_2$-$C_8$alkenyl, phenyl and a 5 to 6 membered heteroaryl;

wherein the $C_3$-$C_6$cycloalkyl, $C_4$-$C_6$heterocycloalkyl, phenyl or 5 to 6 membered heteroaryl is optionally substituted with one to four substituents independently selected from the group consisting of halogen, lower alkyl, lower alkoxy, cyano, nitro, amino, (lower alkyl)amino and di(lower alkyl) amino;

A is selected from the group consisting of N and $CR_5$; wherein $R_5$ is selected from the group consisting of hydrogen, halogen, hydroxyl, lower alkyl, halogenated lower alkyl, lower alkoxy, halogenated lower alkoxy, $C_1$-$C_4$alkylthio, amino, (lower alkyl)amino, di(lower alkyl)amino and cyano;

alternatively, A is $CR_5$, and $R_5$ and $R_1$ are taken together with the atoms to which they are bound to form

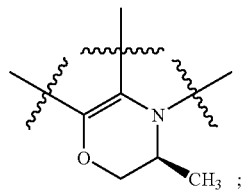

$R_2$ and $R_3$ are each independently selected from the group consisting of hydrogen, halogen, hydroxy, amino, (lower alkyl)amino, di(lower alkyl)amino, lower alkoxy, $C_1$-$C_4$alkylthio, lower alkyl, $C_2$-$C_4$alkenyl and $C_2$-$C_4$alkynyl;

$R_4$ is selected from the group consisting of $C_1$-$C_8$alkyl, —C(O)O-(lower alkyl), aryl, heteroaryl, heterocycloalkyl, —($C_1$-$C_4$alkyl)-$C_3$-$C_6$cycloalkyl, —($C_1$-$C_4$alkyl)-aryl, —($C_1$-$C_4$alkyl)-heteroaryl, and —($C_1$-$C_4$alkyl)-heterocycloalkyl;

wherein the $C_1$-$C_8$alkyl is optionally substituted with one or more substituents independently selected from the group consisting of halogen, hydroxy, amino, (lower alkyl)amino, di(lower alkyl)amino, aryloxy, heteroaryloxy, acyloxy, carboxy, carboxamido, acylamino, oxo, thio, and cyano;

and wherein the aryl, heteroaryl or heterocycloalkyl, whether alone or as part of a substituent group, is optionally substituted with one to three substituents independently selected from the group consisting of halogen, hydroxy, oxo, cyano, mercapto, nitro, amino, (lower alkyl)amino, di(lower alkyl)amino, $C_1$-$C_8$-alkyl, halogenated $C_1$-$C_8$alkyl, $C_1$-$C_8$alkoxy, halogenated $C_1$-$C_8$alkoxy, $C_1$-$C_8$alkylthio, formyl, carboxy, —C(O)O-(lower alkyl), —O—C(O)—($C_1$-

$C_8$-alkyl), —NH—C(O)—($C_1$-$C_8$-alkyl), carboxamide, a second aryl and a second heteroaryl;

and wherein the second aryl or second heteroaryl is optionally substituted with one or more substituents independently selected from the group consisting of halogen, hydroxy, cyano, nitro, amino, (lower alkyl)amino, di(lower alkyl) amino, $C_1$-$C_8$-alkyl, halogenated $C_1$-$C_8$alkyl, $C_1$-$C_8$alkoxy, halogenated $C_{1-8}$alkoxy, $C_1$-$C_8$alkylthio, carboxy and —C(O)O-(lower alkyl);

and optical isomers, diastereomers, enantiomers, pharmaceutically acceptable salts, hydrates, and prodrugs thereof.

Illustrative of the invention is a pharmaceutical composition comprising a pharmaceutically acceptable carrier and the product prepared according to the process described herein. An illustration of the invention is a pharmaceutical composition made by mixing the product prepared according to the process described herein and a pharmaceutically acceptable carrier. Illustrating the invention is a process for making a pharmaceutical composition comprising mixing the product prepared according to the process described herein and a pharmaceutically acceptable carrier.

It has been found that the compounds of this invention, and compositions containing these compounds, are effective antimicrobial agents against a broad range of pathogenic microorganisms with advantages of activity against resistant microbes.

Accordingly, the present invention is also directed to a method of treating a subject having a condition caused by or contributed to by bacterial infection, which comprises administering to said mammal a therapeutically effective amount of the compound of Formula (I).

The present invention is further directed to a method of preventing a subject from suffering from a condition caused by or contributed to by bacterial infection, which comprises administering to the subject a prophylactically effective dose of the pharmaceutical composition of a compound of Formula (I).

The present invention is further directed to the use of a compound of formula (I) for the preparation of a medicament for treating and/or preventing a condition caused by or contributed to by bacteria infection, in a subject in need thereof. In an embodiment, the present invention is directed to the use of a compound of formula (I) for the preparation of a medicament for treating and/or preventing a condition caused by or contributed to by bacteria infection associated with a drug resistant bacteria, in a subject in need thereof

DETAILED DESCRIPTION OF THE INVENTION

The present invention is directed to compounds of formula (I)

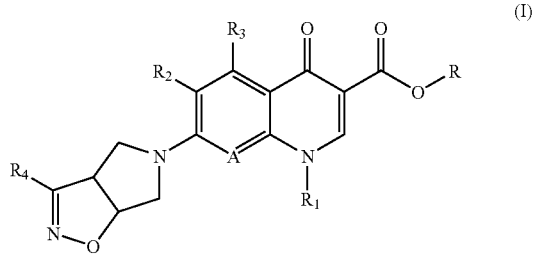

(I)

wherein R, $R_1$, A, $R_2$, $R_3$ and $R_4$ are as herein defined, and optical isomers, diastereomers, enantiomers, pharmaceutically acceptable salts, hydrates, and prodrugs thereof. The compounds of formula (I) are useful as antimicrobial agents against a broad range of pathogenic microorganisms with advantages of activity against resistant microbes.

As used herein, the terms "halo" or "halogen" shall mean fluoro, chloro, bromo or iodo.

As used herein, the prefix "$C_x$-$C_y$" wherein x and y are numbers shall denote the number of carbon atoms present in a particular function group. For example, the term "$C_1$-$C_8$alkyl" denotes any straight or branched chain alkyl as herein define of between 1 and 8 carbon atoms, inclusive. Similarly, the term "$C_2$-$C_4$alkenyl" shall denote an alkenyl group of between 2 and 4 carbon atoms inclusive.

The term "alkyl" shall mean a saturated, straight or branched hydrocarbon chain having 1 to 15 carbons. For example, alkyl radicals include methyl, ethyl, propyl, isopropyl, butyl, isobutyl, sec-butyl, t-butyl, pentyl and the like. Unless otherwise noted, "lower" when used with alkyl means a carbon chain composition of 1-4 carbon atoms.

The term "halogenated alkyl" shall mean any alkyl group as defined above substituted with one to five halogen atoms, preferably with at least one halogen atom, preferably substituted with a least one fluoro atom. Suitable examples include but are not limited to —$CF_3$, —$CH_2$—$CF_3$, —$CF_2$—$CF_2$—$CF_2$—$CF_3$, and the like. Similarly, the term "fluorinated alkyl" shall mean any alkyl group as defined above substituted with one to five fluoro atoms, preferably with at least one fluoro atom. Suitable examples include but are not limited to —$CF_3$, —$CH_2$—$CF_3$, —$CF_2$—$CF_2$—$CF_2$—$CF_3$, and the like.

The terms "alkene" or "alkenyl" shall mean a straight or branched hydrocarbon chain having at least one carbon-carbon double bond and having 2 to 15 carbon atoms. Similarly, the term "Alkyne" shall mean a straight or branched hydrocarbon chain having at least one carbon-carbon triple bond and having 2 to 15 carbon atoms.

The term "alkoxy" shall denote an oxygen ether radical of the above described straight or branched chain alkyl groups (i.e. a group of the formula —O-alkyl). For example, methoxy, ethoxy, n-propoxy, sec-butoxy, t-butoxy, n-hexyloxy and the like. Unless otherwise noted, "lower" when used with alkoxy means an oxygen ether radical as defined above of 1-4 carbon atoms.

The term "halogenated alkoxy" shall mean any alkoxy group as defined above substituted with one to five halogen atoms, preferably with at least one halogen atom, preferably substituted with a least one fluoro atom. Suitable examples include but are not limited to —$OCF_3$, —$OCH_2$—$CF_3$, —$OCF_2$—$CF_2$—$CF_2$—$CF_3$, and the like. Similarly, the term "fluorinated alkoxy" shall mean any alkoxy group as defined above substituted with one to five fluoro atoms, preferably with at least one halogen atom, preferably substituted with a least one fluoro atom. Suitable examples include but are not limited to —$OCF_3$, —$OCH_2$—$CF_3$, —$OCF_2$—$CF_2$—$CF_2$—$CF_3$, and the like.

The term "alkylthio" shall mean —S-alkyl. Suitable examples include but are not limited to methylthio, (—S—$CH_3$), ethyl-thio, isopropyl-thio, and the like.

The term "$C_3$-$C_6$cycloalkyl" shall mean any stable 3-6 membered monocyclic, saturated ring system. Suitable examples include cyclopropyl, cyclobutyl, cyclopentyl, and cyclohexyl. Further, wherein the cycloalkyl is optionally substituted, said substitution may be at any of the carbon atoms of the cycloalkyl group.

The term "aryl" shall refer to unsubstituted carbocyclic aromatic groups such as phenyl, naphthyl, and the like.

The term "heteroaryl" shall denote any five or six membered monocyclic aromatic ring structure containing at least one heteroatom selected from the group consisting of O, N and S, optionally containing one to three additional heteroatoms independently selected from the group consisting of O, N and S; or a nine or ten membered bicyclic aromatic ring structure containing at least one heteroatom selected from the group consisting of O, N and S, optionally containing one to four additional heteroatoms independently selected from the group consisting of O, N and S. The heteroaryl group may be attached at any heteroatom or carbon atom of the ring such that the result is a stable structure. Unless otherwise noted, the heteroaryl group may be optionally substituted with one or more substituents as herein defined.

Examples of suitable heteroaryl groups include, but are not limited to, pyrrolyl, furyl, thienyl, oxazolyl, imidazolyl, pyrazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzothiazolyl, purinyl, quinolinyl, isoquinolinyl, isothiazolyl, cinnolinyl, phthalazinyl, quinazolinyl, quinoxalinyl, naphthyridinyl, pteridinyl, and the like. Preferred heteroaryl groups include, but are not limited to pyridyl, quinolinyl and isoquinolinyl.

The term "heterocycloalkyl" shall denote any five to seven membered monocyclic, saturated or partially unsaturated ring structure containing at least one heteroatom selected from the group consisting of O, N and S, optionally containing one to three additional heteroatoms independently selected from the group consisting of O, N and S; or a nine to ten membered saturated, partially unsaturated or partially aromatic bicyclic ring system containing at least one heteroatom selected from the group consisting of O, N and S, optionally containing one to four additional heteroatoms independently selected from the group consisting of O, N and S. The heterocycloalkyl group may be attached at any heteroatom or carbon atom of the ring such that the result is a stable structure. Unless otherwise noted, the heterocycloalkyl group may be optionally substituted with one or more substituents as herein defined.

Examples of substituted and unsubstituted heterocycloalkyl groups include, but are not limited to, pyrrolinyl, pyrrolidinyl, dioxolanyl, imidazolinyl, imidazolidinyl, pyrazolinyl, pyrazolidinyl, piperidinyl, dioxanyl, morpholinyl, dithianyl, thiomorpholinyl, piperazinyl, trithianyl, indolinyl, chromenyl, 3,4-methylenedioxyphenyl, 2,3-dihydrobenzofuryl, phthalimido (also known as isoindole-1,3-dione), isoindolinyl, and the like. Preferred heterocycloalkyl groups include, but are not limited to phthalimido.

The term "heteroaryloxy" shall mean a group of the formula —O-heteroaryl, wherein the heteroaryl group is as defined above. Suitable examples include, but are not limited to 2-pyridyloxy-2-pyrimidinyl-oxy- and pyridazinyl-oxy-.

The term "acyl" shall mean an organic radical having 2 to 6 carbon atoms (straight chain or branched) derived from an organic acid by removal of the hydroxyl. Suitable examples include but are not limited to acetyl, propionyl and the like. The term "acyloxy" shall mean a group of the formula —O-acyl, wherein the acyl group is as defined above. Suitable examples include but are not limited to acetoxy, propionoxy, and the like.

Unless specified otherwise, it is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques known in the art as well as those methods set forth herein. One skilled in the art will further recognize that substituents may be bound to any of the atoms of a particular group (including, but not limited to C, N or S atoms), provided that the substitution results in a stable structure and does not violate valence rules.

Some of the compounds of the present invention may have trans and cis isomers. In addition, where the processes for the preparation of the compounds according to the invention give rise to mixture of stereoisomers, these isomers may be separated by conventional techniques such as preparative chromatography. The compounds may be prepared as a single stereoisomer or in racemic form as a mixture of some possible stereoisomers. The non-racemic forms may be obtained by either synthesis or resolution. The compounds may, for example, be resolved into their component enantiomers by standard techniques, such as the formation of diastereomeric pairs by salt formation. The compounds may also be resolved by covalent linkage to a chiral auxiliary, followed by chromatographic separation and/or crystallographic separation, and removal of the chiral auxiliary. Alternatively, the compounds may be resolved using chiral chromatography.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at a diastereomeric excess of greater than or equal to about 80%, more preferably, at a diastereomeric excess of greater than or equal to about 90%, more preferably still, at a diastereomeric excess of greater than or equal to about 95%, more preferably still, at a diastereomeric excess of greater than or equal to about 98%, most preferably, at a diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

Under standard nomenclature used throughout this disclosure, the terminal portion of the designated side chain is described first, followed by the adjacent functionality toward the point of attachment. Thus, for example, a "phenylC$_1$-C$_6$alkylaminocarbonylC$_1$-C$_6$alkyl" substituent refers to a group of the formula

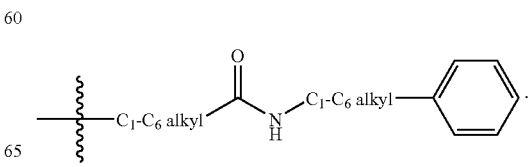

One skilled in the art will recognize that wherein the compounds of formula (I) A is CR$_5$ and R$_1$ and R$_5$ are taken together to form

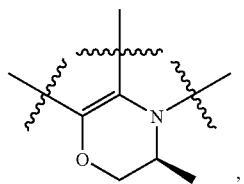

(when unbound to the rest of the compound of formula (I), known as 3S-methyl-3,4-dihydro-2H-[1,4]oxazine, and which is fused to the compound of formula (I) through the 4-, 5- and 6-positions of the oxazine) then the corresponding compounds, hereinafter collectively referred to as compounds of formula (I-C), are of the following structure:

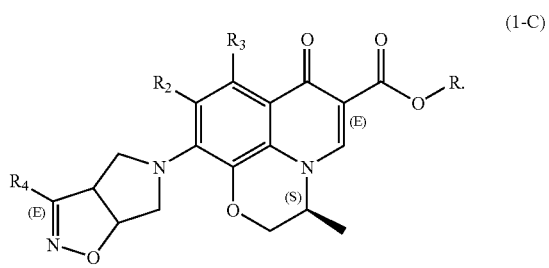

Abbreviations used in the specification, particularly the Schemes and Examples, are as follows:

| | |
|---|---|
| Cbz = | Benzyloxycarbonyl |
| DCE = | Dichloroethane |
| DCM = | Dichloromethane |
| DIAD = | Diisopropylazodicarboxylate |
| DIBAL or DIBAL-H = | Diisobutyl Aluminum Hydride |
| DIPEA or DIEA = | Diisopropylethylamine |
| DMF = | N,N-Dimethylformamide |
| DMSO = | Dimethylsulfoxide |
| HPLC = | High Pressure Liquid Chromatography |
| IPA = | Isopropyl Alcohol |
| PPh3 = | Triphenylphosphine |
| t-BOC or Boc = | Tert-Butoxycarbonyl |
| TEA = | Triethylamine |
| TFA = | Trifluoroacetic Acid |
| THF = | Tetrahydrofuran |

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

The term "prophylactically effective amount" as used herein, means that amount of active compound or pharmaceutical agent that prevents the development of a condition, symptoms or manifestations thereof associated with bacterial infection. Thus it elicits the biological or medicinal response in a tissue system, animal or human that is being sought by a researcher, veterinarian, medical doctor or other clinician, which includes alleviation of the symptoms of the disease or disorder being treated.

The term "drug-resistant" or "drug-resistance" refers to the characteristics of a microbe to survive in the presence of a currently available antimicrobial agent such as an antibiotic at its routine, effective concentration.

As used herein, the term "composition" is intended to encompass a product comprising the specified ingredients in the specified amounts, as well as any product which results, directly or indirectly, from combinations of the specified ingredients in the specified amounts.

One skilled in the art will recognize that, where not otherwise specified, the reaction step(s) is performed under suitable conditions, according to known methods, to provide the desired product.

One skilled in the art will recognize that, in the specification and claims as presented herein, wherein a reagent or reagent class/type (e.g. base, solvent, etc.) is recited in more than one step of a process, the individual reagents are independently selected for each reaction step and may be the same or different from each other. For example wherein two steps of a process recite an organic or inorganic base as a reagent, the organic or inorganic base selected for the first step may be the same or different than the organic or inorganic base of the second step.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis*, John Wiley &

Sons, 1991. The protecting groups may be removed at a convenient subsequent stage using methods known from the art.

The present invention includes within its scope prodrugs of the compounds of this invention. In general, such prodrugs will be functional derivatives of the compounds that are readily convertible in vivo into the required compound. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

For use in medicine, the salts of the compounds of this invention refer to non-toxic "pharmaceutically acceptable salts." Other salts may, however, be useful in the preparation of compounds according to this invention or of their pharmaceutically acceptable salts. Suitable pharmaceutically acceptable salts of the compounds include acid addition salts which may, for example, be formed by mixing a solution of the compound with a solution of a pharmaceutically acceptable acid such as hydrochloric acid, sulfuric acid, fumaric acid, maleic acid, succinic acid, acetic acid, benzoic acid, citric acid, tartaric acid, carbonic acid or phosphoric acid. Furthermore, where the compounds of the invention carry an acidic moiety, suitable pharmaceutically acceptable salts thereof may include alkali metal salts, e.g., sodium or potassium salts; alkaline earth metal salts, e.g., calcium or magnesium salts; and salts formed with suitable organic ligands, e.g., quaternary ammonium salts. Thus, representative pharmaceutically acceptable salts include the following:

acetate, benzenesulfonate, benzoate, bicarbonate, bisulfate, bitartrate, borate, bromide, calcium edetate, camsylate, carbonate, chloride, clavulanate, citrate, dihydrochloride, edetate, edisylate, estolate, esylate, fumarate, gluceptate, gluconate, glutamate, glycollylarsanilate, hexylresorcinate, hydrabamine, hydrobromide, hydrochloride, hydroxynaphthoate, iodide, isothionate, lactate, lactobionate, laureate, malate, maleate, mandelate, mesylate, methylbromide, methylnitrate, methylsulfate, mucate, napsylate, nitrate, N-methylglucamine ammonium salt, oleate, pamoate (embonate), palmitate, pantothenate, phosphate/diphosphate, polygalacturonate, salicylate, stearate, sulfate, subacetate, succinate, tannate, tartrate, teoclate, tosylate, triethiodide and valerate.

Representative acids and bases that may be used in the preparation of pharmaceutically acceptable salts include the following:

acids including acetic acid, 2,2-dichloroacetic acid, acylated amino acids, adipic acid, alginic acid, ascorbic acid, L-aspartic acid, benzenesulfonic acid, benzoic acid, 4-acetamidobenzoic acid, (+)-camphoric acid, camphorsulfonic acid, (+)-(1S)-camphor-10-sulfonic acid, capric acid, caproic acid, caprylic acid, cinnamic acid, citric acid, cyclamic acid, dodecylsulfuric acid, ethane-1,2-disulfonic acid, ethanesulfonic acid, 2-hydroxy-ethanesulfonic acid, formic acid, fumaric acid, galactaric acid, gentisic acid, glucoheptonic acid, D-gluconic acid, D-glucuronic acid, L-glutamic acid, α-oxo-glutaric acid, glycolic acid, hippuric acid, hydrobromic acid, hydrochloric acid, (+)-L-lactic acid, (±)-DL-lactic acid, lactobionic acid, maleic acid, (−)-L-malic acid, malonic acid, (±)-DL-mandelic acid, methanesulfonic acid, naphthalene-2-sulfonic acid, naphthalene-1,5-disulfonic acid, 1-hydroxy-2-naphthoic acid, nicotinic acid, nitric acid, oleic acid, orotic acid, oxalic acid, palmitic acid, pamoic acid, phosphoric acid, L-pyroglutamic acid, salicylic acid, 4-amino-salicylic acid, sebacic acid, stearic acid, succinic acid, sulfuric acid, tannic acid, (+)-L-tartaric acid, thiocyanic acid, p-toluenesulfonic acid and undecylenic acid; and bases including ammonia, L-arginine, benethamine, benzathine, calcium hydroxide, choline, deanol, diethanolamine, diethylamine, 2-(diethylamino)-ethanol, ethanolamine, ethylenediamine, N-methyl-glucamine, hydrabamine, 1H-imidazole, L-lysine, magnesium hydroxide, 4-(2-hydroxyethyl)-morpholine, piperazine, potassium hydroxide, 1-(2-hydroxyethyl)-pyrrolidine, sodium hydroxide, triethanolamine, tromethamine and zinc hydroxide.

In an embodiment of the present invention, R is selected from the group consisting of hydrogen, methyl, ethyl and t-butyl. In another embodiment of the present invention, R is hydrogen.

In an embodiment of the present invention, $R_1$ is selected from the group consisting of $C_{3-6}$cycloalkyl, $C_{4-6}$heterocycloalkyl, phenyl, and 6 membered heteroaryl; wherein the $C_{3-6}$cycloalkyl, $C_{4-6}$heterocycloalkyl, phenyl or 6 membered heteroaryl is optionally substituted with one to three substituents independently selected from the group consisting of halogen, lower alkyl, lower alkoxy, cyano, amino, (lower alkyl)amino and di(lower alkyl)amino.

In another embodiment of the present invention, $R_1$ is selected from the group consisting of $C_3$-$C_6$cycloalkyl, phenyl, and 6 membered heteroaryl; wherein the $C_3$-$C_6$cycloalkyl, phenyl or 6 membered heteroaryl is optionally substituted with one to three substituents independently selected from the group consisting of halogen and amino. In another embodiment of the present invention, $R_1$ is selected from the group consisting of cyclopropyl, 2,4-difluorophenyl, 1R-(2S-fluoro-cyclopropyl) and 2-(3,5-difluoro-6-amino-pyridyl). In another embodiment of the present invention, $R_1$ is selected from the group consisting of cyclopropyl, 2,4-difluorophenyl and 1R-(2S-fluoro-cyclopropyl).

In an embodiment of the present invention, A is selected from the group consisting of N and $CR_5$; wherein $R_5$ is selected from the group consisting of hydrogen, halogen, lower alkyl, fluorinated lower alkyl, lower alkoxy and fluorinated lower alkoxy. In another embodiment of the present invention, A is selected from the group consisting of N and $CR_5$; wherein $R_5$ is selected from the group consisting of hydrogen, halogen, lower alkoxy and fluorinated lower alkoxy. In another embodiment of the present invention, A is selected from the group consisting of N and $CR_5$; wherein $R_5$ is selected from the group consisting of hydrogen, chloro, methoxy and difluoromethoxy. In another embodiment of the present invention, A is selected from the group consisting of N and $CR_5$; wherein $R_5$ is selected from the group consisting of hydrogen and methoxy.

In an embodiment of the present invention, A is $CR_5$, and $R_5$ and $R_1$ are taken together with the atoms to which they are bound to form

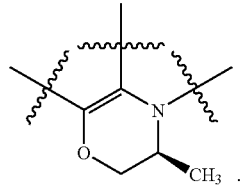

In an embodiment of the present invention, A is N. In an embodiment of the present invention, A is $CR_5$; wherein $R_5$ is selected from the group consisting of hydrogen, halogen, lower alkyl, fluorinated lower alkyl, lower alkoxy and fluorinated lower alkoxy. In another embodiment of the present invention, A is $CR_5$; wherein $R_5$ is selected from the group consisting of hydrogen, halogen, lower alkoxy and fluorinated lower alkoxy. In another embodiment of the present invention, A is $CR_5$; wherein $R_5$ is selected from the group consisting of hydrogen, chloro, methoxy and difluoromethoxy. In another embodiment of the present invention, A is $CR_5$; wherein $R_5$ is selected from the group consisting of hydrogen and methoxy.

In an embodiment of the present invention, $R_2$ and $R_3$ are each independently selected from the group consisting of hydrogen, halogen, hydroxy, amino, (lower alkyl)amino, di(lower alkyl)amino, lower alkyl and lower alkoxy. In an embodiment of the present invention, $R_2$ is halogen. In another embodiment of the present invention, $R_2$ is fluoro. In an embodiment of the present invention, $R_3$ is hydrogen.

In an embodiment of the present invention, $R_4$ is selected from the group consisting of lower alkyl, —C(O)O-(lower alkyl), aryl, heteroaryl, heterocycloalkyl, —($C_1$-$C_2$alkyl)-heteroaryl and —($C_1$-$C_2$alkyl)-heterocycloalkyl; wherein the lower alkyl is optionally substituted with one to two substituents independently selected from the group consisting of halogen, hydroxy, amino, (lower alkyl)amino, di(lower alkyl)amino, aryloxy, heteroaryloxy, acyloxy, carboxy, oxo and cyano; wherein the aryl, heteroaryl or heterocycloalkyl, whether alone or as part of a substituent group is optionally substituted with one to two substituents independently selected from the group consisting of halogen, hydroxy, cyano, amino, (lower alkyl)amino, di(lower alkyl)amino, lower alkyl, halogenated lower alkyl, lower alkoxy, halogenated lower alkoxy, oxo, carboxy and —C(O)O-(lower alkyl). In another embodiment of the present invention, $R_4$ is selected from the group consisting of lower alkyl, —C(O)O-(lower alkyl), aryl, heteroaryl, heterocycloalkyl and —($C_1$-$C_2$alkyl)-heteroaryl; wherein the lower alkyl is optionally substituted with one to two substituent independently selected from the group consisting of halogen, hydroxy, amino, (lower alkyl)amino, di(lower alkyl)amino, aryloxy, heteroaryloxy, acyloxy, carboxy, oxo and cyano; wherein the aryl, heteroaryl or heterocycloalkyl, whether alone or as part of a substituent group is optionally substituted with one to two substituents independently selected from the group consisting of halogen, hydroxy, cyano, amino, (lower alkyl)amino, di(lower alkyl)amino, lower alkyl, halogenated lower alkyl, lower alkoxy, halogenated lower alkoxy, oxo, carboxy and —C(O)O-(lower alkyl). In another embodiment of the present invention, $R_4$ is selected from the group consisting of lower alkyl, phenyl, 6 membered heteroaryl, 2-(isoindole-1, 3-dione)-methyl-, and —C(O)O-lower alkyl; wherein the lower alkyl is optionally substituted with a substituent selected from the group consisting of hydroxy and amino; and wherein the phenyl or 6 membered heteroaryl is optionally substituted with a substituent selected from the group consisting of halogen, lower alkoxy and fluorinated lower alkyl.

In an embodiment of the present invention, $R_4$ is selected from the group consisting of ethoxy-carbonyl-, hydroxy-methyl-, amino-methyl-, 4-chlorophenyl, 4-methoxy-phenyl, 2-(isoindole-1,3-dione)-methyl-, 2-pyridyl, 3-pyridyl, 4-pyridyl, 3-(6-methoxy-pyridyl) and 3-(6-trifluoromethyl-pyridyl). In another embodiment of the present invention, $R_4$ is selected from the group consisting of 4-chlorophenyl, 4-methoxy-phenyl, 2-pyridyl, 3-pyridyl, 4-pyridyl, 3-(6-methoxy-pyridyl) and 3-(6-trifluoromethyl-pyridyl). In another embodiment of the present invention, $R_4$ is selected from the group consisting of 4-chlorophenyl, 4-methoxyphenyl, 2-pyridyl and 3-pyridyl.

In an embodiment, the present invention is directed to compound selected from the group consisting of 7-[3-(4-chloro-phenyl)-3a,4,6,6a-tetrahydro-pyrrolo[3,4-d]isoxazol-5-yl]-1-(2,4-difluoro-phenyl)-6-fluoro-4-oxo-1,4-dihydro-[1,8]naphthyridine-3-carboxylic acid; 1-(2,4-difluoro-phenyl)-6-fluoro-4-oxo-7-(3-pyridin-3-yl-3a,4,6,6a-tetrahydro-pyrrolo[3,4-d]isoxazol-5-yl)-1,4-dihydro-[1,8] naphthyridine-3-carboxylic acid; 1-cyclopropyl-6-fluoro-4-oxo-7-(3-pyridin-3-yl-3a,4,6,6a-tetrahydro-pyrrolo[3,4-d] isoxazol-5-yl)-1,4-dihydro-[1,8]naphthyridine-3-carboxylic acid; 1-cyclopropyl-6-fluoro-8-methoxy-7-[3-(4-methoxy-phenyl)-3a,4,6,6a-tetrahydro-pyrrolo[3,4-d]isoxazol-5-yl]-4-oxo-1,4-dihydro-quinoline-3-carboxylic acid; 6-fluoro-1R-(2S-fluoro-cyclopropyl)-8-methoxy-7-[3-(4-methoxy-phenyl)-3a,4,6,6a-tetrahydro-pyrrolo[3,4-d]isoxazol-5-yl]-4-oxo-1,4-dihydro-quinoline-3-carboxylic acid; 8-fluoro-9-[3-(4-methoxy-phenyl)-3a,4,6,6a-tetrahydro-pyrrolo[3,4-d] isoxazol-5-yl]-3S-methyl-6-oxo-2,3-dihydro-6H-1-oxa-3a-aza-phenalene-5-carboxylic acid; 1-cyclopropyl-6-fluoro-4-oxo-7-(3-pyridin-2-yl-3a,4,6,6a-tetrahydro-pyrrolo[3,4-d] isoxazol-5-yl)-1,4-dihydro-quinoline-3-carboxylic acid; and optical isomers, diastereomers, enantiomers, pharmaceutically acceptable salts, hydrates, and prodrugs thereof.

Additional embodiments of the present invention, include those wherein the substituents selected for one or more of the variables defined herein (i.e. R, $R_1$, A, $R_2$, $R_3$, and $R_4$) are independently selected to be any individual substituent or any subset of substituents selected from the complete list as defined herein.

In another embodiment of the present invention is any single compound or subset of compounds selected from the representative compounds listed in Tables 1 and 2, below.

Representative compounds of the present invention are as listed in Table 1-3, below. For clarity, the hyphen ("-") at the end of a substituent group name indicates the bonding point of the substituent group to the rest of the compound of formula (I). Similarly, for the A substituent, the ">C—" symbol indicates that A is $CR_5$, with the C atom bound into the ring structure of the compound of formula (I). Unless otherwise noted, wherein a stereogenic center is present, an S- or R-designation is indicated, however, the exact optical rotation of the compound was not determined, although the compound was prepared using chiral reagents wherein the desired stereoconfiguration was present in an enantiomeric excess.

TABLE 1

Representative Compounds of Formula (I)

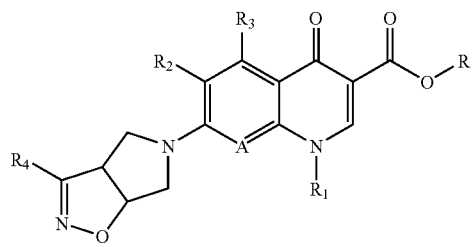

| ID No. | R | $R_1$ | A | $R_2$ | $R_3$ | $R_4$ |
|---|---|---|---|---|---|---|
| 101 | H | 2,4-difluorophenyl | N | F | H | 4-chlorophenyl |
| 102 | H | 2,4-difluorophenyl | N | F | H | 3-(6-methoxy-pyridyl) |

TABLE 1-continued

Representative Compounds of Formula (I)

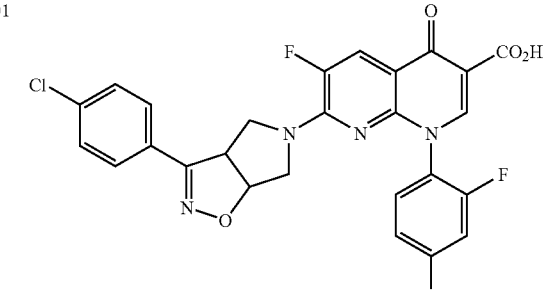

| ID No. | R | R₁ | A | R₂ | R₃ | R₄ |
|---|---|---|---|---|---|---|
| 103 | H | 2,4-difluorophenyl | N | F | H | 3-(6-trifluoromethyl-pyridyl) |
| 104 | H | 2,4-difluorophenyl | N | F | H | 2-pyridyl |
| 105 | H | 2,4-difluorophenyl | N | F | H | 3-pyridyl |
| 106 | H | 2,4-difluorophenyl | N | F | H | ethoxy-carbonyl- |
| 107 | H | 2,4-difluorophenyl | N | F | H | hydroxy-methyl- |
| 108 | H | 2,4-difluorophenyl | N | F | H | 2-(isoindole-1,3-dione)-methyl- |
| 200 | H | 2,4-difluorophenyl | N | F | H | amino-methyl- |
| 110 | H | cyclopropyl | N | F | H | 4-chlorophenyl |
| 111 | H | cyclopropyl | N | F | H | 3-(6-methoxy-pyridyl) |
| 112 | H | cyclopropyl | N | F | H | 3-(6-trifluoromethyl-pyridyl) |
| 113 | H | cyclopropyl | N | F | H | 2-pyridyl |
| 114 | H | cyclopropyl | N | F | H | 3-pyridyl |
| 115 | H | cyclopropyl | N | F | H | 4-pyridyl |
| 116 | H | cyclopropyl | N | F | H | ethoxy-carbonyl- |
| 117 | H | cyclopropyl | N | F | H | hydroxy-methyl- |
| 118 | H | cyclopropyl | N | F | H | 2-(isoindole-1,3-dione)-methyl- |
| 201 | H | cyclopropyl | N | F | H | amino-methyl- |
| 120 | H | cyclopropyl | >C—OCH₃ | F | H | 4-methoxy-phenyl |
| 121 | H | cyclopropyl | >C—OCH₃ | F | H | 3-(6-trifluoromethyl-pyridyl) |
| 122 | H | cyclopropyl | >C—OCH₃ | F | H | 2-pyridyl |
| 123 | H | cyclopropyl | >C—OCH₃ | F | H | 3-pyridyl |
| 124 | H | cyclopropyl | >C—OCH₃ | F | H | ethoxy-carbonyl- |
| 125 | H | cyclopropyl | >C—OCH₃ | F | H | 2-(isoindole-1,3-dione)-methyl- |
| 202 | H | cyclopropyl | >C—OCH₃ | F | H | amino-methyl- |
| 126 | H | 1R-(2S-fluoro-cyclopropyl) | >C—OCH₃ | F | H | 4-methoxy-phenyl |
| 127 | H | 1R-(2S-fluoro-cyclopropyl) | >C—OCH₃ | F | H | 2-(isoindole-1,3-dione)-methyl- |
| 203 | H | 1R-(2S-fluoro-cyclopropyl) | >C—OCH₃ | F | H | amino-methyl- |
| 133 | H | 2-(3,5-difluoro-6-amino-pyridyl) | >C—Cl | F | H | 4-methoxy-phenyl |
| 134 | H | cyclopropyl | >CH | F | H | 3-(6-methoxy-pyridyl) |
| 135 | H | cyclopropyl | >CH | F | H | 2-pyridyl |
| 136 | H | cyclopropyl | >CH | F | H | 3-pyridyl |
| 137 | H | cyclopropyl | >C—OCF₂H | F | H | 2-(isoindole-1,3-dione)-methyl- |
| 150 | H | cyclopropyl | >C—OCH₃ | H | H | 2-pyridyl |

TABLE 2

Representative Compounds of Formula (I)

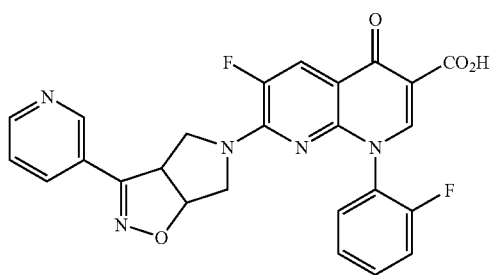

| ID No. | R | R₂ | R₃ | R₄ |
|---|---|---|---|---|
| 128 | H | F | H | 4-methoxy-phenyl |
| 129 | H | F | H | 2-pyridyl |
| 130 | H | F | H | 3-pyridyl |
| 131 | H | F | H | ethoxycarbonyl- |
| 132 | H | F | H | 2-(isoindole-1,3-dione)-methyl- |
| 204 | H | F | H | amino-methyl- |

In an embodiment, the present invention is directed to any single compound or subset of compounds selected from the representative compounds of formula (I) listed in Table 3, below.

TABLE 3

Representative Compounds of Formula (I)

| ID No. | Structure |
|---|---|
| 101 | (7-[3-(4-Chloro-phenyl)-3a,4,6,6a-tetrahydro-pyrrolo[3,4-d]isoxazol-5-yl]-1-(2,4-difluoro-phenyl)-6-fluoro-4-oxo-1,4-dihydro-[1,8]naphthyridine-3-carboxylic acid) |
| 105 | 1-(2,4-Difluoro-phenyl)-6-fluoro-4-oxo-7-(3-pyridin-3-yl-3a,4,6,6a-tetrahydro-pyrrolo[3,4-d]isoxazol-5-yl)-1,4-dihydro-[1,8]naphthyridine-3-carboxylic acid |

TABLE 3-continued

Representative Compounds of Formula (I)

| ID No. | Structure |
|---|---|
| 114 | 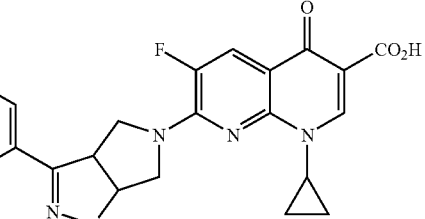<br>1-Cyclopropyl-6-fluoro-4-oxo-7-(3-pyridin-3-yl-3a,4,6,6a-tetrahydro-pyrrolo[3,4-d]isoxazol-5-yl)-1,4-dihydro-[1,8]naphthyridine-3-carboxylic acid |
| 120 | 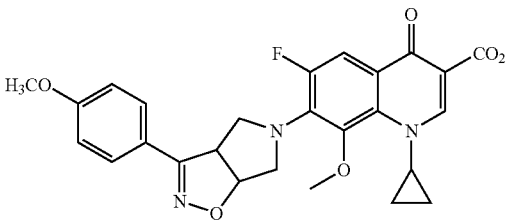<br>1-Cyclopropyl-6-fluoro-8-methoxy-7-[3-(4-methoxy-phenyl)-3a,4,6,6a-tetrahydro-pyrrolo[3,4-d]isoxazol-5-yl]-4-oxo-1,4-dihydro-quinoline-3-carboxylic acid |
| 126 | 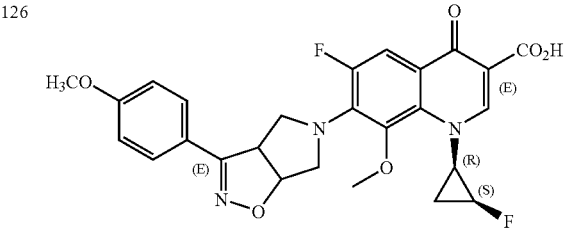<br>6-Fluoro-1R-(2S-fluoro-cyclopropyl)-8-methoxy-7-[3-(4-methoxy-phenyl)-3a,4,6,6a-tetrahydro-pyrrolo[3,4-d]isoxazol-5-yl]-4-oxo-1,4-dihydro-quinoline-3-carboxylic acid |
| 128 | 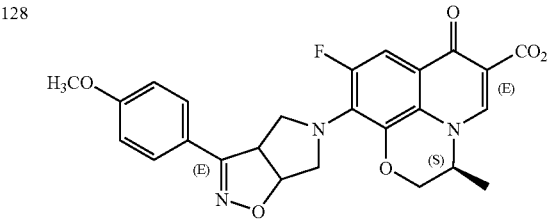<br>8-Fluoro-9-[3-(4-methoxy-phenyl)-3a,4,6,6a-tetrahydro-pyrrolo[3,4-d]isoxazol-5-yl]-3S-methyl-6-oxo-2,3-dihydro-6H-1-oxa-3a-aza-phenalene-5-carboxylic acid |
| 135 | 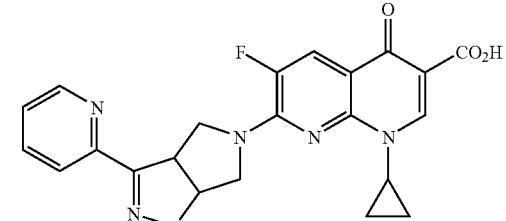<br>1-Cyclopropyl-6-fluoro-4-oxo-7-(3-pyridin-2-yl-3a,4,6,6a-tetrahydro-pyrrolo[3,4-d]isoxazol-5-yl)-1,4-dihydro-quinoline-3-carboxylic acid |

In an embodiment, the present invention is directed to compounds of formula (I) whose MIC (minimal inhibitory concentration) against strain A as measured according to the procedure described in Example 84 The micro should be 84 is less than or equal to or equal to about 0.25 µg/mL, preferably less than or equal to or equal to about 0.12 µg/mL, more preferably less than or equal to about 0.06 µg/mL.

In an embodiment, the present invention is directed to compounds of formula (I) whose MIC (minimal inhibitory concentration) against strain B as measured according to the procedure described in Example 84 is less than or equal to or equal to about 16 µg/mL, preferably less than or equal to or equal to about 8 µg/mL, more preferably less than or equal to about 4 µg/mL.

In an embodiment, the present invention is directed to compounds of formula (I) whose MIC (minimal inhibitory concentration) against strain C as measured according to the procedure described in Example 84 is less than or equal to or equal to about 16 µg/mL, preferably less than or equal to or equal to about 8 µg/mL, more preferably less than or equal to about 4 µg/mL.

In an embodiment, the present invention is directed to compounds of formula (I) whose MIC (minimal inhibitory concentration) against strain D as measured according to the procedure described in Example 84 is less than or equal to or equal to about 16 µg/mL, preferably less than or equal to or equal to about 8 µg/mL, more preferably less than or equal to about 4 µg/mL.

In an embodiment, the present invention is directed to compounds of formula (I) whose MIC (minimal inhibitory concentration) against strain E as measured according to the procedure described in Example 84 is less than or equal to or equal to about 4 µg/mL, preferably less than or equal to or equal to about 2 µg/mL, more preferably less than or equal to about 1 µg/mL.

General Reaction Schemes for Compound Preparation

In making the compounds of the invention, the order of synthetic steps may be varied to increase the yield of desired product. In addition, the skilled artisan will also recognize the judicious choice of reactions, solvents, and temperatures are an important component in successful synthesis. While the determination of optimal conditions, etc. is routine, it will be understood that a variety of compounds can be generated in a similar fashion, using the guidance of the schemes below.

The starting materials used in preparing the compounds of the invention are known, made by published synthetic methods or available from commercial vendors.

It is recognized that the skilled artisan in the art of organic chemistry can readily carry out standard manipulations of the organic compounds without further direction; that is, it is well within the scope and practice of the skilled artisan to carry out such manipulations. These include, but are not limited to, reductions of carbonyl compounds to their corresponding alcohols, oxidations, acylations, aromatic substitutions, both electrophilic and nucleophilic, etherifications, esterification and saponification and the like. Examples of these manipulations are discussed in standard texts such as March, *Advanced Organic Chemistry* (Wiley), Carey and Sundberg, *Advanced Organic Chemistry* (Vol. 2), Feiser & Feiser, *Reagents for Organic Synthesis* (16 volumes), L. Paquette, *Encyclopedia of Reagents for Organic Synthesis* (8 volumes), Frost & Fleming, *Comprehensive Organic Synthesis* (9 volumes) and the like.

The skilled artisan will readily appreciate that certain reactions are best carried out when other functionality is masked or protected in the molecule, thus avoiding any undesirable side reactions and/or increasing the yield of the reaction. Often the skilled artisan utilizes protecting groups to accomplish such increased yields or to avoid the undesired reactions. Examples of these manipulations can be found for example in T. Greene, *Protecting Groups in Organic Synthesis*.

General procedures for preparing heterocyclic nuclei useful in making the compounds of the invention are described in the following references, all incorporated by reference herein (including articles listed within the references): U.S. Pat. No. 6,329,391, European Patent Publication 342849, International Patent Publication WO9711068, European Patent Publication 195316, European Patent Publication 1031569, U.S. Pat. No. 6,025,370, European Patent Publication 153828, European Patent Publication 191451, European Patent Publication 153163, European Patent Publication 230053, European Patent Publication 976749, International Patent Publication WO0118005, International Patent Publication WO9407873, U.S. Pat. No. 4,777,253, European Patent Publication 421668, International Patent Publication WO0248138, European Patent Publication 230295, International Patent Publication WO9914214, U.S. Patent Publication 20020049223, International Patent Publication WO9921849, International Patent Publication WO9729102, International Patent Publication WO0334980, International Patent Publication WO0209758, International Patent Publication WO9619472, German Patent Publication DE 3142854, International Patent Publication WO0334980, International Patent Publication WO0328665, European Patent Publication 47005, International Patent Publication WO0311450, and European Patent Publication 688772.

Synthetic Schemes

Compounds of formula (I) may be prepared according to the process outlined in Scheme 1 below.

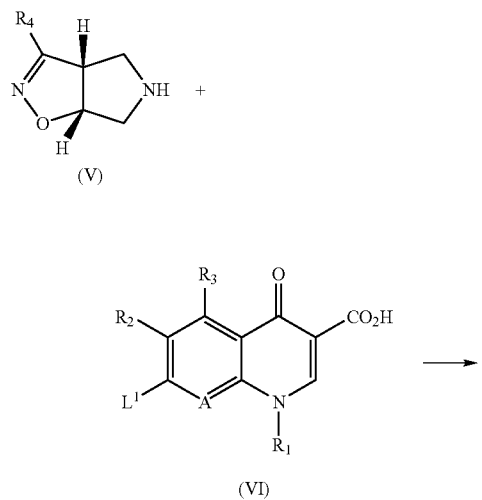

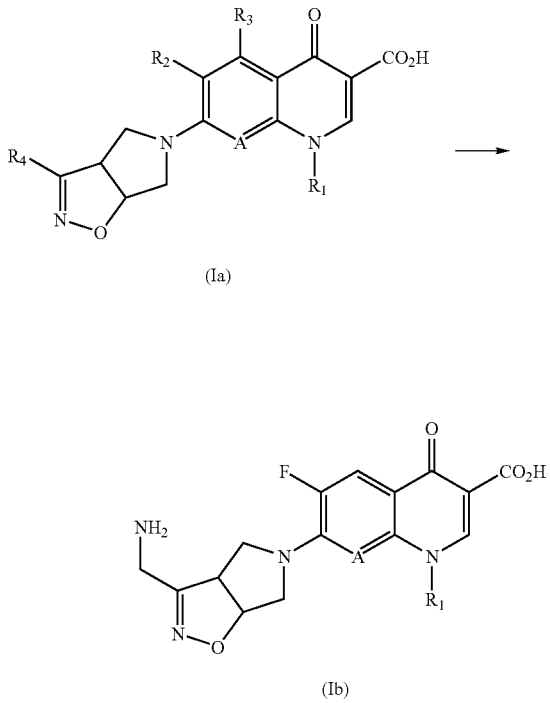

Accordingly, a suitably substituted compound of formula (V), as a free base or its corresponding acid addition salt, for example its corresponding TFA salt, a known compound or compound prepared according to known methods, or compound prepared according to the processes as described in Schemes 4 and 5 herein, is reacted with a suitably substituted compound of formula (VI), wherein $L^1$ is a suitably selected leaving group such as Cl, F, and the like, a known compound or compound prepared by known methods;

in the presence of an organic base such as TEA, DIPEA, pyridine, and the like; in an organic solvent such as acetonitrile, DMSO, N-methylpyrrolidinone, DMF, and the like; preferably at a temperature greater than about room temperature, more preferably at a temperature in the range of from about 55 to about 100° C., to yield the corresponding compound of formula (Ia).

One skilled in the art will recognize that wherein the compound of formula (Ia), $R_4$ is N-phthalimidomethyl, the compound of formula (Ia) may be further reacted with hydrazine ($NH_2NH_2$), a known compound, in an organic solvent such as ethanol, methanol, isopropanol, and the like, preferably at a temperature greater than about room temperature, more preferably at a temperature in the range of from about 65 to about 83° C., to yield the corresponding compound of formula (Ib). One skilled in the art will recognize that compounds of formula (Ib) may be prepared using suitably selected nitrogen protecting groups other than phthalimide, which nitrogen protecting groups may be removed according to known methods, following the reaction of compound of formula (V) with compound of formula (VI) to yield compound of formula (Ia).

Compounds of formula (I) wherein A is N or $CR_5$, and wherein $R_5$ is lower alkoxy, may alternatively be prepared according to the process outlined in Scheme 2 below.

Scheme 2

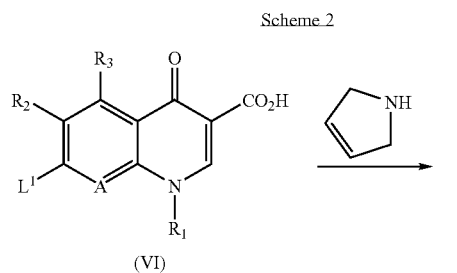
(VI)

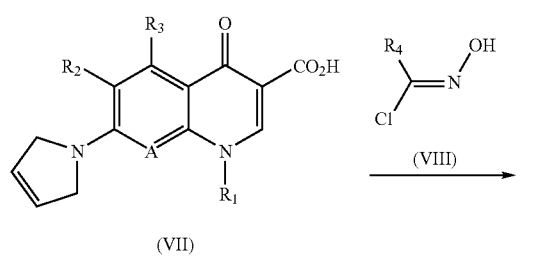
(VII)

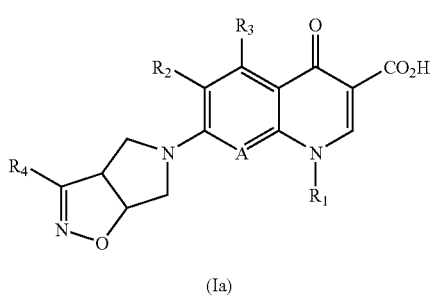
(Ia)

Accordingly, a suitably substituted compound of formula (VI), wherein $L^1$ is a suitably selected leaving group such as Cl, F, and the like, a known compound or compound prepared according to known methods, is reacted with 2,5-dihydro-1H-pyrrole, a known compound;

in the presence of an organic base such as TEA, DIPEA, pyridine, and the like; in an organic solvent such as acetonitrile, DMSO, N-methylpyrrolidinone, DMF, and the like; preferably at a temperature greater than about room temperature, more preferably at a temperature in the range of from about 55 to about 100° C., to yield the corresponding compound of formula (VII).

The compound of formula (VII) is reacted with a suitably substituted compound of formula (VIII), a known compound or compound prepared according to known methods, in the presence of an inorganic base such as $NaHCO_3$, $KHCO_3$, and the like, in an organic solvent such as IPA, ethyl acetate, and the like; preferably at a temperature greater than about room temperature, more preferably at a temperature in the range of from about 25 to about 40° C., to yield the corresponding compound of formula (Ia).

Compounds of formula (I) may alternatively be prepared according to the process outlined in Scheme 3 below. This process is particularly useful for the preparation of compounds of formula (I) wherein A is $CR_5$ and $R_5$ is lower alkoxy, halogenated lower alkoxy, or alternatively wherein $R_1$ and $R_5$ are taken together with the atoms to which they are bound to form a structure of the following formula

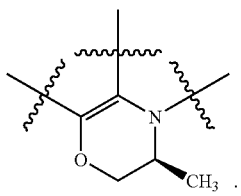

In the process outlined in Scheme 3 below, the conversion of the —$CO_2H$ substituent on the compound of formula (VI) to the corresponding —$CO_2BF_2$ substituent group results in an increase in the reactivity of the compound of formula (VI) to nucleophilic addition with a suitably substituted amine. One skilled in the art will recognize that alternate activating groups may also be used such as esters, boron acetate esters, and the like, according to known methods.

Scheme 3

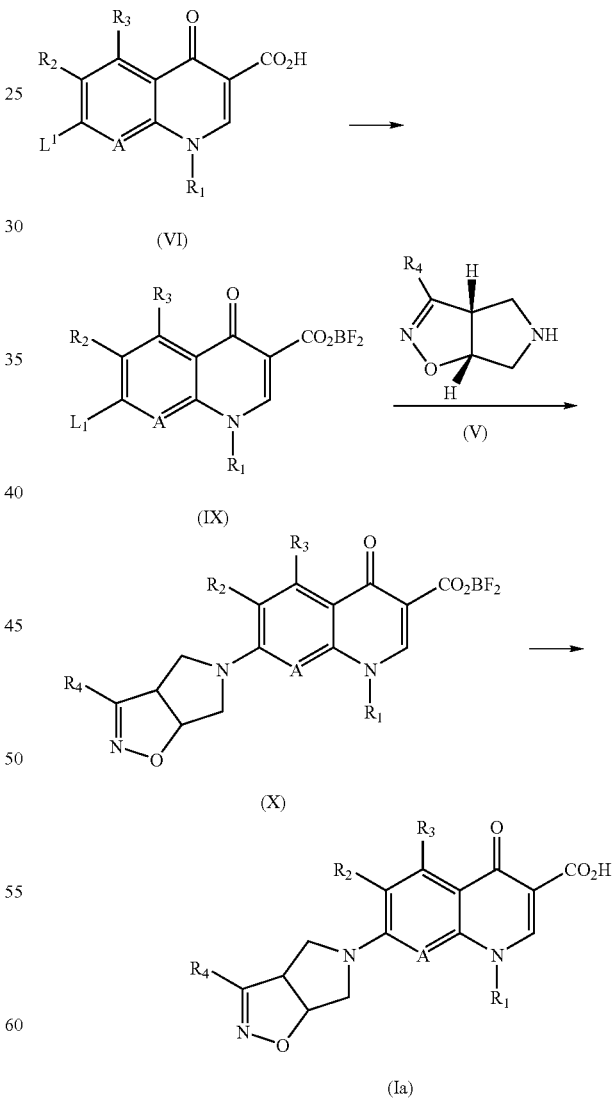

Accordingly, a suitably substituted compound of formula (VI), wherein $L^1$ is a suitably selected leaving group such as Cl, F, and the like, a known compound or compound prepared according to known methods, is reacted with BF₃.O(CH₂CH₃)₂, a known compound;

in an organic solvent such as THF, diethyl ether, and the like; preferably at a temperature greater than about room temperature, more preferably at a temperature in the range of from about 35 to about 66° C., to yield the corresponding compound of formula (IX).

The compound of formula (IX) is reacted with a suitably substituted compound of formula (V), as a free base or its corresponding acid addition salt, for example its corresponding TFA salt, a known compound or compound prepared according to known methods, or compound prepared according to the processes as described in Schemes 4 and 5 herein;

in the presence of an organic base such as TEA, DIPEA, pyridine, and the like; in an organic solvent such as acetonitrile, DMSO, DMF, N-methylpyrrolidinone, and the like; preferably at a temperature greater than about room temperature, more preferably at a temperature in the range of from about 55 to about 100° C., to yield the corresponding compound of formula (X).

The —CO₂BF₂ substituent on compound of formula (X) is then converted to its corresponding —CO₂H substituent by reacting the compound of formula (X) with an organic base such as TEA, DIPEA, and the like, in an organic solvent such as ethanol, methanol, isopropanol, and the like, preferably at a temperature greater than about room temperature, more preferably at a temperature in the range of from about 65 to about 83° C., to yield the corresponding compound of formula (Ia).

One skilled in the art will recognize, that as discussed in relation to the process outlined in Scheme 1, wherein the compound of formula (Ia) R₄ is a protected amine, said amine may be de-protected according to known methods.

Compounds of formula (I) wherein R is other than hydrogen may be prepared according to the process outlined in Scheme 1 above, by reacting a compound of formula (V) with a compound of formula (VI-EST)

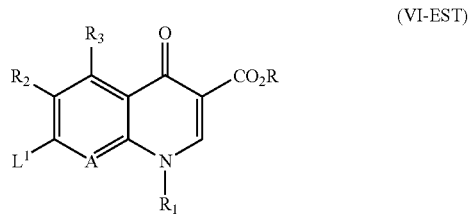

(VI-EST)

wherein R is lower alkyl and wherein the compound of formula (VI-EST) is the corresponding alkyl ester of the compound of formula (VI) as defined herein.

Compounds of formula (V) may be prepared according to the process outlined in Scheme 4, below.

Scheme 4

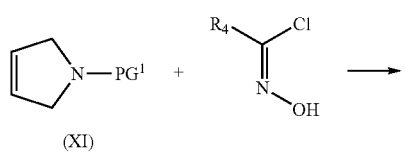

(XI)

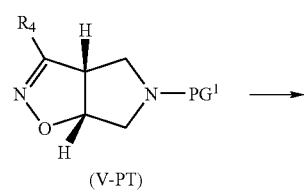

(V-PT)

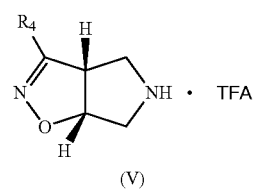

(V)

Accordingly, a compound of formula (XI), wherein PG¹ is a suitably selected nitrogen protecting group such as BOC, Cbz, trifluoroacetyl, and the like, a known compound or compound prepared by known methods, is reacted with a suitably selected compound of formula (VIII), wherein R₄ is a group such as aryl, heteroaryl and the like, a known compound or compound prepared by known methods;

in the presence of an organic or inorganic base such as TEA, DIPEA, pyridine, NaHCO₃, KHCO₃, Na₂CO₃, K₂CO₃, and the like, in an organic solvent such as ethyl acetate, diethyl ether, and the like, at room temperature or in an organic solvent such as IPA, 2-butanol, and the like, at a temperature in the range of from about 25 to about 40° C.; to yield the corresponding compound of formula (V-PT), a compound or formula (V) wherein the NH group is substituted with a suitably selected nitrogen protecting group.

The compound of formula (V-PT) may be de-protected according to known methods, for example by reacting with a suitably selected acid such as TFA, HCl, and the like, in an organic solvent such as DCM, DCE, isopropanol, chloroform, and the like, to yield the corresponding compound of formula (V), as its corresponding acid addition salt.

Compounds of formula (V) wherein R₄ is —CO₂-lower alkyl, —CH₂—OH or —CH₂-phthalimide may alternatively be prepared according to the process outlined in Scheme 5, below.

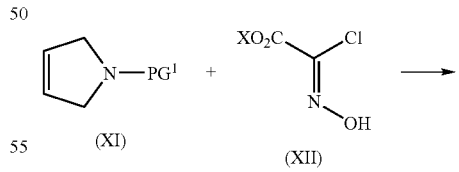

(XI)        (XII)

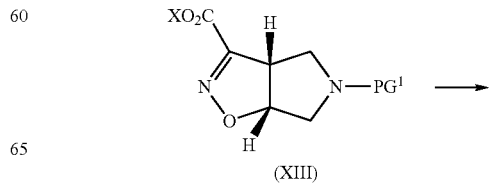

(XIII)

-continued

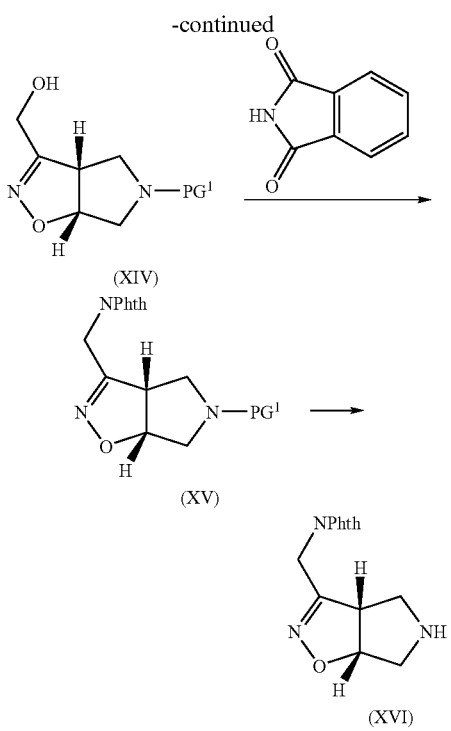

(XIV)

(XV)

(XVI)

Accordingly, a suitably substituted compound of formula (XI), wherein $PG^1$ is a suitably selected nitrogen protecting group such as BOC, Cbz, trifluoroacetyl, and the like, a known compound or compound prepared by known methods, is reacted with a suitably selected compound of formula (XII), wherein X is lower alkyl, a known compound or compound prepared by known methods;

in the presence of an organic or inorganic base such as TEA, DIPEA, pyridine, $NaHCO_3$, $KHCO_3$, $Na_2CO_3$, $K_2CO_3$, and the like, in an organic solvent such as ethyl acetate, diethyl ether, and the like, at room temperature or in an organic solvent such as IPA, 2-butanol, and the like, at a temperature in the range of form about 25 to about 40° C.; to yield the corresponding compound of formula (XIII) (a compound of formula (V) wherein $R_4$ is $—CO_2$-lower alkyl and wherein the nitrogen group is protected with $PG^1$ a suitably selected nitrogen protecting group).

The compound of formula (XIII) is reacted with a suitably selected reducing agent such as $NaBH_4$, lithium borohydride, DIBAL, and the like, in an organic solvent such as ethanol, methanol, THF, and the like, to yield the corresponding compound of formula (XIV) (a compound of formula (V) wherein $R_4$ is $—CH_2—OH$ and wherein the nitrogen group is protected with $PG^1$ a suitably selected nitrogen protecting group).

The compound of formula (XIV) is reacted to convert the $—OH$ group on the compound of formula (XIV) to a corresponding protected amine. For example, the compound of formula (XIV) is converted via a Mitsunobu reaction by combining with phthalimide, in the presence of a DIAD and $PPh_3$, in an organic solvent such as THF, dioxane, and the like, to yield the corresponding compound of formula (XV).

The compound of formula (XV) may be further de-protected according to known methods, to yield the corresponding compound of formula (XVI). One skilled in the art will further recognize that the compound of formula (XIII) and/or the compound of formula (XIV) may also be de-protected according to known methods, for example by reacting with a suitably selected acid such as TFA, HCl, and the like, in an organic solvent such as DCM, DCE, isopropanol, chloroform, and the like, to yield the corresponding compounds of formula (XVII) and (XVIII) respectively, as their corresponding acid addition salts

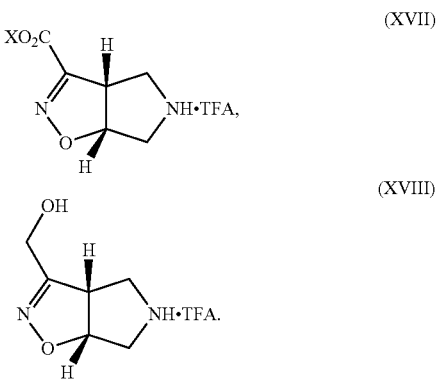

The present invention further comprises pharmaceutical compositions containing one or more compounds of formula (I) with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gel caps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1-5000 mg or any range therein, and may be given at a dosage of from about 0.01-50 mg/kg/day, or any range therein, preferably from about 1.0-30 mg/kg/day, or any range therein. The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, autoinjector devices or suppositories; for oral, parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form yielding the advantage of prolonged action. For example, the tablet or pill can comprise an inner dosage and an outer dosage component, the latter being in the form of an envelope over the former. The two components can be separated by an enteric layer, which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The methods described in the present invention may also be carried out using a pharmaceutical composition comprising any of the compounds as defined herein and a pharmaceutically acceptable carrier. The pharmaceutical composition may contain between about 0.01 mg and 5000 mg of the compound, or any range therein; preferably about 70 to 2000 mg of the compound, or any range therein, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders, lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms may include suitably flavored suspending or dispersing agents such as the synthetic and natural gums, for example, tragacanth, acacia, methyl-cellulose and the like. For parenteral administration, sterile suspensions and solutions are desired. Isotonic preparations, which generally contain suitable preservatives, are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phosphatidylcholine.

Compounds of the present invention may also be delivered by the use of monoclonal antibodies as individual carriers to which the compound molecules are coupled. The compounds of the present invention may also be coupled with soluble polymers as target able drug carriers. Such polymers can include polyvinylpyrrolidone, pyran copolymer, polyhydroxypropylmethacrylamidephenol, polyhydroxy-ethylaspartamidephenol, or polyethyleneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyric acid, polyorthoesters, polyacetals, polydihydropyrans, polycyanoacrylates and cross-linked or amphipathic block copolymers of hydrogels.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

Compounds of this invention may be administered in any of the foregoing compositions and according to dosage regimens established in the art whenever treatment with antimicrobial agents is required.

The daily dosage of the products may be varied over a wide range from 0.01 to 5,000 mg per adult human per day, or any range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 50 mg/kg of body weight per day, or any range therein. Preferably, the range is from about 0.5 to about 40 mg/kg of body weight per day, or any range therein. More preferably, from about 1.0 to about 30 mg/kg of body weight per day, or any range therein. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trails including first-in-human, dose ranging and efficacy trials, in healthy patients and/or those suffering from a given disorder, may be completed according to methods well known in the clinical and medical arts.

EXAMPLES

The following Examples are set forth to aid in the understanding of the invention, and are not intended and should not be construed to limit in any way the invention set forth in the claims which follow thereafter.

In the Examples that follow, some synthesis products are listed as having been isolated as a residue. It will be understood by one of ordinary skill in the art that the term "residue" does not limit the physical state in which the product was isolated and may include, for example, a solid, an oil, a foam, a gum, a syrup, and the like.

Preparation of Oximes and Chloro Oximes

Some oximes were commercially available and were used without further purification. For those that weren't commercially available, they were prepared according to the procedures as described in Examples 1-12 below.

Example 1

4-Chlorobenzaldehyde oxime (1a)

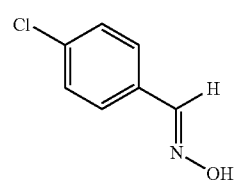

1a

4-Chlorobenzaldehyde (45.6 g; 0.325 mol), hydroxylamine hydrochloride (27.9 g; 0.401 mol) and pyridine (64 mL; 0.791 mol) in methylene chloride (600 mL) were stirred overnight at room temperature. The reaction mixture was poured into aqueous hydrochloric acid (2N; 300 mL) and extracted. The organic layer was washed with additional aqueous hydrochloric acid (2×300 mL), water (300 mL), dried (MgSO$_4$), filtered and evaporated to yield oxime 1a as a white solid.

MS 156 (M+H).

Example 2

4-Methoxybenzaldehyde oxime (1b)

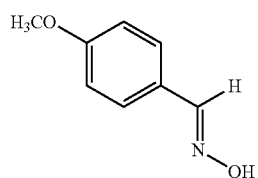

1b

The title compound was prepared in an analogous manner to 4-chlorobenzaldehyde oxime (1a). 1b was isolated as a white solid.

MS 152 (M+H).

Example 3

6-Methoxy-pyridine-3-carboxaldehyde oxime (1c)

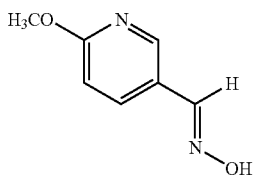

The title compound was prepared in an analogous manner to 4-chlorobenzaldehyde oxime (1a). 1c was isolated as white crystals.

MS 153 (M+H).

Example 4

6-Trifluoromethyl-pyridine-3-carboxaldehyde oxime (1d)

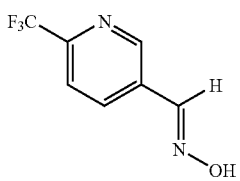

The title compound was prepared in an analogous manner to 4-chlorobenzaldehyde oxime (1a). 1d was isolated as white crystals.

MS 191 (M+H).

Example 5

Pyridine-2-carboxaldehyde oxime (1e)

To a solution of pyridine-2-carboxaldehyde (5.5 mL; 57.8 mmol) in ethanol (100 mL) at 0° C., was added water (22 mL) and hydroxylamine hydrochloride (5.32 g; 76.6 mmol). Aqueous sodium hydroxide (1N; 50 mL) was added dropwise and the reaction mixture warmed to room temperature overnight. The reaction mixture was poured into water (250 mL) and extracted with ethyl acetate (3×150 mL). The combined organic layers were washed with water (100 mL), dried ($MgSO_4$), filtered and evaporated to yield oxime 1e as a white solid.

MS 122 (M+H).

Example 6

4-Chloro-N-hydroxy-benzenecarboximidoyl chloride (2a)

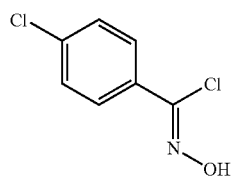

The title compound was prepared according to the method of Howe and Shelton (J Org Chem. 1980, 45, 3916). 2a was isolated as a white solid.

Example 7

4-Methoxy-N-hydroxybenzenecarboximidoyl chloride (2b)

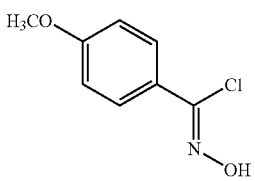

The title compound was prepared according to the method of Howe and Shelton. 2b was isolated as a white solid.

Example 8

N-Hydroxy-6-methoxy-3-pyridinecarboximidoyl chloride (2c)

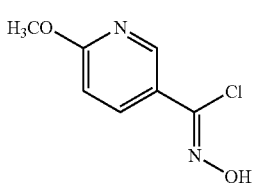

To oxime 1c (1.25 g; 8.18 mmol) in concentrated hydrochloric acid (6.0 mL) at 0° C., was added dropwise bleach (9 mL). The reaction mixture was stirred at 0° C. for 1 h, diluted with water (20 mL) and brought to about pH=3 with saturated sodium bicarbonate. The resulting solid was collected, washed with water and dried. 2c was isolated as a white solid.

Example 9

N-Hydroxy-6-trifluoromethyl-3-pyridinecarboximidoyl chloride (2d)

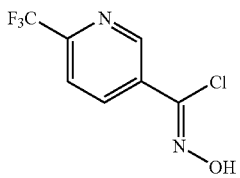

2d

The title compound was prepared in an analogous manner to the 4-methoxy-3-pyridyl case 2c using a suitably substituted oxime. 2d was isolated as an aqua solid.

Example 10

N-Hydroxy-2-pyridinecarboximidoyl chloride (2e)

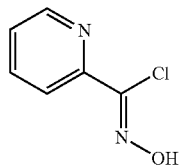

2e

The title compound was prepared in an analogous manner to the 4-methoxy-3-pyridyl case 2c using a suitably substituted oxime. 2e was isolated as a white solid.

Example 11

N-Hydroxy-3-pyridinecarboximidoyl chloride (2f)

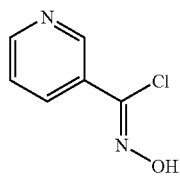

2f

The title compound was prepared in an analogous manner to the 4-methoxy-3-pyridyl case 2c using a suitably substituted oxime. 2f was isolated as a cream-colored solid.

Example 12

N-Hydroxy-4-pyridinecarboximidoyl chloride (2g)

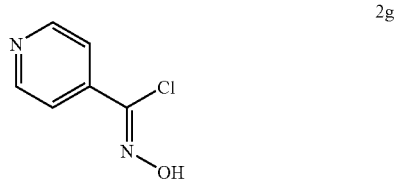

2g

The title compound was prepared in an analogous manner to the 4-methoxy-3-pyridyl case 2c using a suitably substituted oxime. 2g was isolated as a white solid.

Preparation and Elaboration of Cycloadducts

Examples 13-21 describe the preparation of representative cycloadducts.

Example 13 cis-3-(4-Chlorophenyl)-3a,4,6,6a-tetrahydro-pyrrolo[3,4-d]isoxazole-5-carboxylic acid tert-butyl ester (3a)

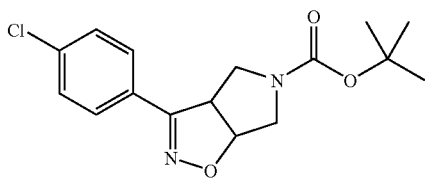

3a

To N-Boc pyrroline (480 mg; 2.83 mmol) and chloro oxime 2a (557 mg; 2.93 mmol) in ethyl acetate (15 mL), was added dropwise triethylamine (0.4 mL) in ethyl acetate (15 mL). The reaction mixture was stirred at room temperature for 24 hours. An additional portion of chloro oxime 2a (234 mg; 1.23 mmol) and triethylamine were added. After stirring overnight, the reaction mixture was poured into water (50 mL) and extracted. The organic layer was dried (MgSO$_4$), filtered and evaporated. Chromatography with 30% ethyl acetate/hexanes yielded 3a as a white solid.

MS 345 (M+Na).

Example 14 cis-3-(4-Methoxyphenyl)-3a,4,6,6a-tetrahydro-pyrrolo[3,4-d]isoxazole-5-carboxylic acid tert-butyl ester (3b)

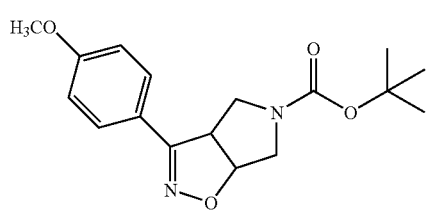

3b

The title compound was prepared in an analogous manner as the 4-chlorophenyl cycloadduct 3a using chloro oxime 2b. However, two additional portions of chloro oxime and triethyl amine were used. 3b was isolated as a white solid.

MS 341 (M+Na).

Example 15 cis-3-(6-Methoxypyridin-3-yl) 3a,4,6,6a-tetrahydro-pyrrolo[3,4-d]isoxazole-5-carboxylic acid tert-butyl ester (3c)

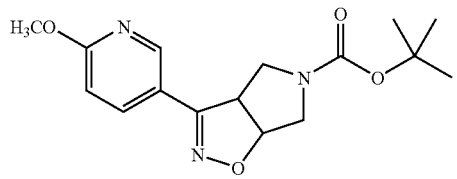

3c

Chloro oxime 2c (1.12 g; 5.99 mmol), N-Boc-pyrroline (0.5 mL; 2.90 mmol) and sodium bicarbonate (0.61 g) in ethyl acetate (40 mL) were stirred at room temperature for 24 hours. The reaction mixture was diluted with ethyl acetate and washed with water. The organic layer was dried (MgSO$_4$), filtered and evaporated to yield crude cycloadduct. 3c was isolated as a white solid after chromatography with 25% ethyl acetate/hexanes.

MS 320 (M+H).

Example 16 cis-3-(6-Trifluoromethylpyridin-3-yl) 3a,4,6,6a-tetrahydro-pyrrolo[3,4-d]isoxazole-5-carboxylic acid tert-butyl ester (3d)

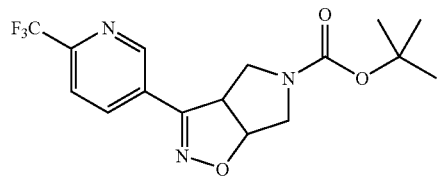

3d

The title compound was prepared in an analogous manner as the 4-methoxy-3-pyridyl cycloadduct 3c using chloro oxime 2d. 3d was isolated as a white solid after chromatography with 25% ethyl acetate/hexanes.

MS 358 (M+H).

Example 17 cis-3-(Pyridin-2-yl)-3a,4,6,6a-tetrahydro-pyrrolo[3,4-d]isoxazole-5-carboxylic acid tert-butyl ester (3e)

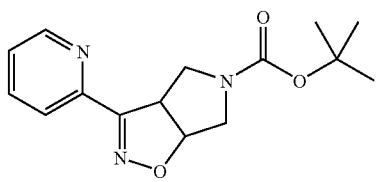

3e

The title compound was prepared in an analogous manner as the 4-methoxy-3-pyridyl cycloadduct 3c using chloro oxime 2e. 3e was isolated as a white solid after chromatography with 1.5% methanol/methylene chloride.

MS 290 (M+H).

Example 18 cis-3-(Pyridin-3-yl)-3a,4,6,6a-tetrahydro-pyrrolo[3,4-d]isoxazole-5-carboxylic acid tert-butyl ester (3f)

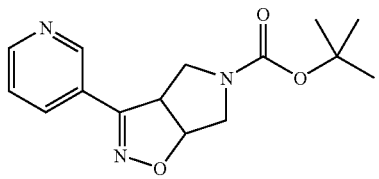

3f

N-Boc pyrroline (270 mg; 1.60 mmol), chloro oxime 2f (470 mg; 3.00 mmol) and sodium bicarbonate (760 mg; 9.04 mmol) in isopropanol (10 mL) were heated at 40° C. overnight. An additional portion of chloro oxime and sodium bicarbonate was added and heating continued for 20 hours.

After cooling, the volatiles were evaporated. The residue was dissolved in ethyl acetate (50 mL), and washed with water (50 mL). The organic layer was dried (MgSO$_4$), filtered and evaporated. Cycloadduct 3f was isolated as a beige powder after chromatography with 70% ethyl acetate/hexanes.

MS 290 (M+H).

Example 19 cis-3a,4,6,6a-Tetrahydropyrrolo[3,4-d]isoxazole-3,5-dicarboxylic acid 5-tert-butyl ester-3-ethyl ester (6)

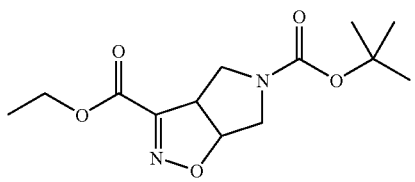

6

The title compound was prepared using commercially available ethyl chloro oximidoacetate (5). N-Boc-pyrroline (1.0 g; 5.91 mmol), ethyl chloro oximidoacetate (2.55 g; 16.8 mmol) and sodium bicarbonate (1.77 g; 21.06 mmol) in ethyl acetate (15 mL) were stirred for 54 hours. An additional amount of chloro oxime (2.6 g; 17.28 mmol) and sodium bicarbonate (2.1 g; 25.00 mmol) was added and the reaction mixture stirred overnight. The addition of reagents was repeated again and the reaction mixture stirred for 36 hours. The reaction mixture was diluted with ethyl acetate and washed with water. The organic layer was washed with water, brine, dried (MgSO$_4$), filtered and evaporated. Cycloadduct 6 was isolated as a clear oil after chromatography with 20% ethyl acetate/hexanes.

MS 307 (M+Na).

Example 20 cis-3-Hydroxymethyl-3a,4,6,6a-tetrahydropyrrolo[3,4-d]isoxazole-5-carboxylic acid tert-butyl ester (7)

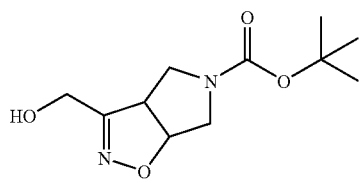

7

To ester 6 (1.50 g; 5.29 mmol) in ethanol (50 mL) at 0° C., was added sodium borohydride (1.57 g; 41.5 mmol) in several portions. The reaction mixture was stirred at 0° C. for 30 minutes and then at room temperature for 3 hours. The reaction mixture was carefully added to water (150 mL) and extracted with methylene chloride (3×100 mL). The combined organic layers were washed with several portions of water, brine, dried (MgSO$_4$), filtered and evaporated to yield alcohol 7 as a white solid.

MS 265 (M+Na).

Example 21 cis-3-(1,3-Dioxo-1,3-dihydro-isoindol-2-ylmethyl)-3a,4,6,6a-tetrahydro-pyrrolo[3,4-d]isoxazole-5-carboxylic acid tert-butyl ester (8)

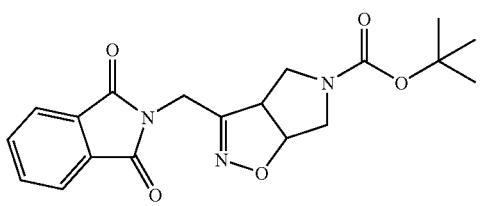

8

To alcohol 7 (1.13 g; 4.67 mmol), triphenyl phosphine (1.28 g; 4.88 mmol) and phthalimide (0.73 g; 4.96 mmol) in THF (75 mL) was added DIAD (0.98 mL; 4.94 mmol). The reaction mixture was stirred at room temperature overnight. The volatiles were evaporated and the residue chromatographed with 50% ethyl acetate/hexanes to yield phthalimide 8 as a white foam.

MS394(M+Na).

Removal of the Boc-Protecting Group

Examples 22-30 describe removal of the t-butoxy-carbonyl (BOC) protecting group from the cycloadduct compounds prepared above.

Example 22 cis-3-(4-Chlorophenyl)-4,5,6,6a-tetrahydro-3aH-pyrrolo[3,4-d]isoxazole trifluoroacetate salt (4a)

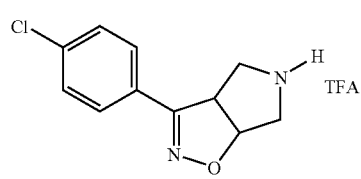

4a

Boc protected amine 3a (200 mg; 0.62 mmol) and trifluoroacetic acid (0.5 mL) in methylene chloride (10 mL) were stirred at room temperature under nitrogen for 18 hours. The volatiles were evaporated. The oily residue was triturated with ether. The resulting solid was collected, washed with additional ether and dried to yield the trifluoroacetate salt of amine 4a as an off-white solid.

MS 223 (M+H).

Example 23 cis-3-(4-Methoxyphenyl)-4,5,6,6a-tetrahydro-3aH-pyrrolo[3,4-d]isoxazole trifluoroacetate salt (4b)

The title compound was prepared in an analogous manner to the 4-chlorophenyl amine 4a above. 4b was isolated as a light brick colored powder.

MS 219 (M+H).

Example 24 cis-3-(6-Methoxy-3-pyridyl)-4,5,6,6a-tetrahydro-3aH-pyrrolo[3,4-d]isoxazole trifluoroacetate salt (4c)

The title compound was prepared in an analogous manner to the 4-chlorophenyl amine 4a. 4c was isolated as an off-white solid.

MS 220 (M+H).

Example 25 cis-3-(6-Trifluoromethyl-3-pyridyl)-4,5,6,6a-tetrahydro-3aH-pyrrolo[3,4-d]isoxazole trifluoroacetate salt (4d)

The title compound was prepared in an analogous manner to the 4-chlorophenyl amine 4a above. 4d was isolated as a white solid.

MS 258 (M+H).

Example 26 cis-3-(2-Pyridyl)-4,5,6,6a-tetrahydro-3aH-pyrrolo[3,4-d]isoxazole trifluoroacetate salt (4e)

The title compound was prepared in an analogous manner to the 4-chlorophenyl amine 4a above. 4e was isolated as a white solid.

MS 190(M+H).

Example 27 cis-3-(3-Pyridyl)-4,5,6,6a-tetrahydro-3aH-pyrrolo[3,4-d]isoxazole trifluoroacetate salt (4f)

The title compound was prepared in an analogous manner to the 4-chlorophenyl amine 4a above. However, trituration did not produce a solid. The salt 4f was isolated as a light brown oil.

MS 190(M+H).

Example 28 cis-4,5,6,6a-Tetrahydro-3aH-pyrrolo[3,4-d]isoxazole-3-carboxylic acid ethyl ester trifluoroacetate salt (10)

The title compound was prepared in an analogous manner to the 4-chlorophenyl amine 4a above. 10 was isolated as a cream-colored solid.

MS 185(M+H).

Example 29 cis-(4,5,6,6a-Tetrahydro-3aH-pyrrolo[3,4-d]isoxazol-3-yl)-methanol trifluoroacetate salt (11)

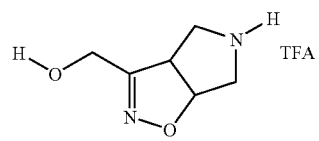

The title compound was prepared in an analogous manner to the 4-chlorophenyl amine 4a above, however, the alcohol 11 was isolated as an oil.

MS 143 (M+H).

Example 30 cis-2-(4,5,6,6a-Tetrahydro-3aH-pyrrolo[3,4-d]isoxazol-3-ylmethyl)-isoindole-1,3-dione trifluoroacetate salt (9)

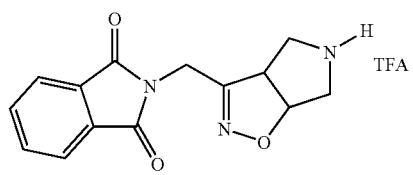

The title compound was prepared in an analogous manner to the 4-chlorophenyl amine 4a above. Phthalimide 9 was isolated as a white solid.

MS 272 (M+H).

Preparation of Heterocyclic Nuclei

The following heterocyclic nuclei were either commercially available as the carboxylic acid or the ethyl ester: 1-cyclopropyl-1,4-dihydro-6,7-difluoro-8-methoxy-4-oxo-quinoline-3-carboxylic acid (52), 7-chloro-1-cyclopropyl-6-fluoro-4-oxo-1,4-dihydro-naphthyridine-3-carboxylic acid (51), 9,10-difluoro-2,3-dihydro-3-methyl-7-oxo-7H-pyrido[1,2,3-de]-1,4-benzoxazine-6-carboxylic acid (54), and 7-chloro-1-(2,4-difluorophenyl)-6-fluoro-4-oxo-1,4-dihydro-naphthyridine-3-carboxylic acid (50). In the case of the ethyl esters, conversion to the corresponding acid was accomplished by a standard hydrolysis reaction.

The following heterocyclic nuclei were prepared according to literature procedures as noted in Examples 31-35, below: 1-cyclopropyl-1,4-dihydro-6,7-difluoro-8-difluoromethoxy-4-oxo-quinoline-3-carboxylic acid (57), 1-cyclopropyl-1,4-dihydro-6,7-difluoro-4-oxo-quinoline-3-carboxylic acid (56), 1-[(1R,2S)-2-fluorocyclopropy]1-1,4-dihydro-6,7-difluoro-8-methoxy-4-oxo-quinoline carboxylic acid (53), 1-(6-amino-3,5-difluoro-2-pyridinyl)-8-chloro-6,7-difluoro-1,4-dihydro-4-oxo-quinoline-3-carboxylic acid (55), 1-cyclopropyl-1,4-dihydro-7-fluoro-8-methoxy-4-oxo-quinoline-3-carboxylic acid (70).

Example 31

1-Cyclopropyl-1,4-dihydro-6,7-difluoro-8-difluoromethoxy-4-oxo-quinoline-3-carboxylic acid (57)

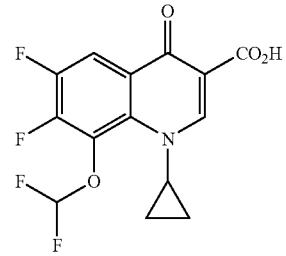

The title compound was prepared according to the method described in U.S. Pat. No. 5,436,367.

Example 32

1-Cyclopropyl-1,4-dihydro-6,7-difluoro-4-oxo-quinoline-3-carboxylic acid (56)

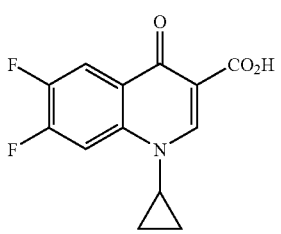

The title compound was prepared according to the method described in EP0342849 A2.

Example 33

1-[(1R,2S)-2-Fluorocyclopropy]1-1,4-dihydro-6,7-difluoro-8-methoxy-4-oxo-quinoline carboxylic acid (53)

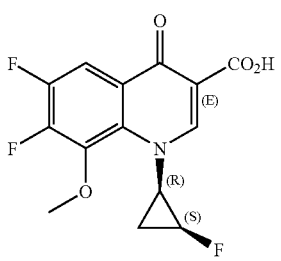

The title compound was prepared according to the method described in WO 01/072738 using the commercially available (−)-(1R,2S)-2-fluorocyclopropylamine tosylate salt.

Example 34

1-(6-amino-3,5-difluoro-2-pyridinyl)-8-chloro-6,7-difluoro-1,4-dihydro-4-oxo-quinoline-3-carboxylic acid (55)

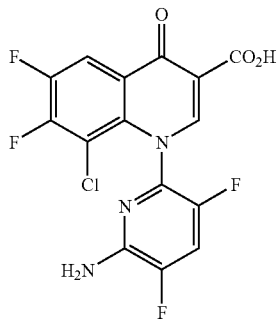

55

The N-1 substituent (monoprotected as the t-butyl amine) was prepared as described in WO97/11068. The keto enol ether was prepared as described in U.S. Pat. No. 4,885,386. Both of these intermediates were then utilized to complete the synthesis of the above compound as described in WO97/11068.

Example 35

1-Cyclopropyl-1,4-dihydro-7-fluoro-8-methoxy-4-oxoquinoline-3-carboxylic acid (70)

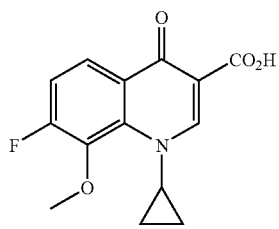

70

The title compound was prepared as described in U.S. Pat. No. 6,329,391.

Preparation of Activated Cores

Examples 36-40 below, describe activation of representative heterocyclic nuclei prepared as described above.

Example 36

1-Cyclopropyl-1,4-dihydro-6,7-difluoro-8-methoxy-4-oxo-quinoline-3-carboxylic acid difluoroborate ester (61)

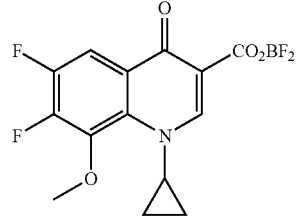

61

Commercially available 1-cyclopropyl-1,4-dihydro-6,7-difluoro-8-methoxy-4-oxo-quinoline-3-carboxylic acid (52) (10.08 g; 34.14 mmol) and boron trifluoride etherate (30 mL; 236 mmol) in anhydrous THF (150 mL) were heated at reflux temperature under a nitrogen atmosphere for 36 hours. After cooling, ether (250 mL) was added. The resulting white solid was collected by filtration, washed with ether and dried to give 1-cyclopropyl-1,4-dihydro-6,7-difluoro-8-methoxy-4-oxo-quinoline-3-carboxylic acid difluoroborate ester (61) as a white solid.

MS 344 (M+H).

Example 37

1-Cyclopropyl-1,4-dihydro-6,7-difluoro-8-difluoromethoxy-4-oxo-quinoline-3-carboxylic acid difluoroborate ester (59)

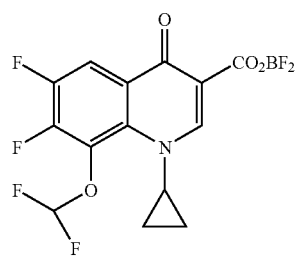

59

The title compound was prepared in a manner analogous to 1-cyclopropyl-1,4-dihydro-6,7-difluoro-8-methoxy-4-oxo-quinoline-3-carboxylic acid difluoroborate ester (61) but starting with 1-cyclopropyl-1,4-dihydro-6,7-difluoro-8-difluoromethoxy-4-oxo-quinoline-3-carboxylic acid to yield 59 as an off-white solid.

MS 380 (M+H).

Example 38

1-[(1R,2S)-2-Fluorocyclopropyl]-1,4-dihydro-6,7-difluoro-8-methoxy-4-oxo-quinoline-3-carboxylic acid difluoroborate ester (60)

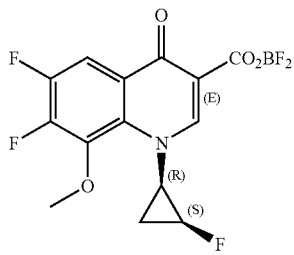

60

The title compound was prepared in a manner analogous to 1-cyclopropyl-1,4-dihydro-6,7-difluoro-8-methoxy-4-oxo-quinoline-3-carboxylic acid difluoroborate ester (61) but starting with 1-[(1R,2S)-2-fluorocyclopropy]1-1,4-dihydro-6,7-difluoro-8-methoxy-4-oxo-quinoline carboxylic acid to yield 60 as a grey solid.

MS 362 (M+H).

Example 39

S-(−)-9,10-difluoro-2,3-dihydro-3-methyl-7-oxo-7H-pyrido-[1,2,3-de][1,4]-benzoxazine-6-carboxylic acid difluoroborate ester (58)

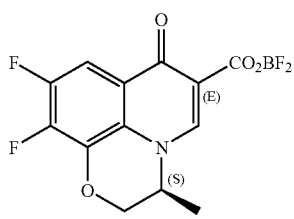

58

The title compound was prepared in an analogous manner as for difluoroborate ester 61, but starting with S-(−)-9,10-difluoro-2,3-dihydro-3-methyl-7-oxo-7H-pyrido-[1,2,3-de][1,4]-benzoxazine-6-carboxylic acid to yield 58 as an off-white powder.

MS 330 (M+H).

Example 40

1-Cyclopropyl-1,4-dihydro-7-fluoro-8-methoxy-4-oxoquinoline-3-carboxylic acid difluoroborate ester (71)

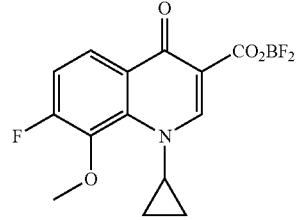

71

The title compound was prepared in an analogous manner as for difluoroborate ester 61, but starting with 1-cyclopropyl-1,4-dihydro-7-fluoro-8-methoxy-4-oxoquinoline-3-carboxylic acid (70) to yield 71 as an off-white powder.

MS 326 (M+H).

Preparation of Final Target Compounds

Examples 41-83 describe the preparation of representative compounds of formula (I).

Example 41

7-[3-(4-Chloro-phenyl)-3a,4,6,6a-tetrahydro-pyrrolo[3,4-d]isoxazol-5-yl]-1-(2,4-difluoro-phenyl)-6-fluoro-4-oxo-1,4-dihydro-[1,8]naphthyridine-3-carboxylic acid (101)

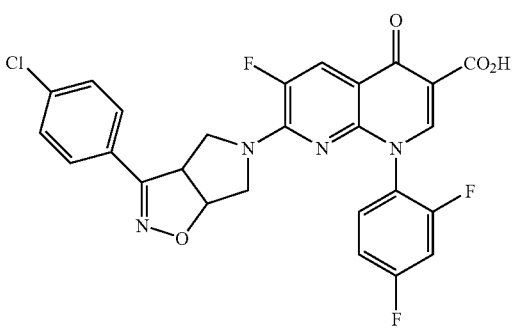

101

7-Chloro-1-(2,4-difluorophenyl-6-fluoro-4-oxo-1,4-dihydronapthyridine-3-carboxylic acid (50) (120 mg; 0.34 mmol), trifluoroacetate salt 4a (131 mg; 0.39 mmol) and triethylamine (0.3 mL) in acetonitrile (3 mL) were heated at reflux temperature overnight. After cooling, the volatiles were evaporated. The residue was triturated with water, filtered and dried to yield acid 101 as an off-white solid.

MS 541 (M+H).

Example 42

1-(2,4-Difluoro-phenyl)-6-fluoro-7-[3-(6-methoxy-pyridin-3-yl)-3a,4,6,6a-tetrahydro-pyrrolo[3,4-d]isoxazol-5-yl]-4-oxo-1,4-dihydro-[1,8]naphthyridine-3-carboxylic acid (102)

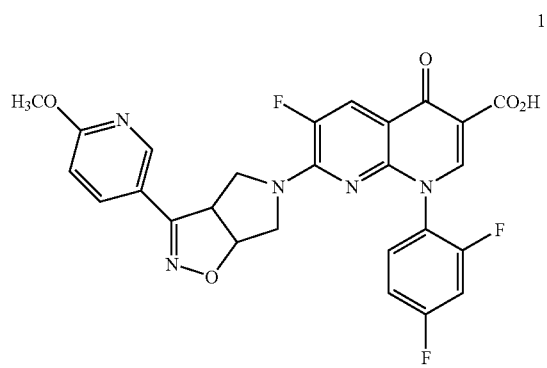

The title compound was prepared in an analogous manner to acid 101, but using TFA salt 4c. Acid 102 was isolated as a tan solid.
MS 538 (M+H).

Example 43

1-(2,4-Difluoro-phenyl)-6-fluoro-4-oxo-7-[3-(6-trifluoromethyl-pyridin-3-yl)-3a,4,6,6a-tetrahydro-pyrrolo[3,4-d]isoxazol-5-yl]-1,4-dihydro-[1,8]naphthyridine-3-carboxylic acid (103)

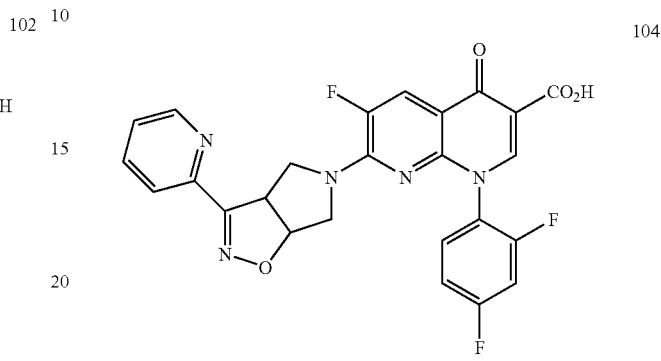

The title compound was prepared in an analogous manner to acid 101, but using a suitably substituted TFA salt 4d. Acid 103 was isolated as a gold solid.
MS 576 (M+H).

Example 44

1-(2,4-Difluoro-phenyl)-6-fluoro-4-oxo-7-(3-pyridin-2-yl-3a,4,6,6a-tetrahydro-pyrrolo[3,4-d]isoxazol-5-yl)-1,4-dihydro-[1,8]naphthyridine-3-carboxylic acid (104)

The title compound was prepared in an analogous manner to acid 101, but using a suitably substituted TFA salt 4e. Acid 104 was isolated as a tan solid.
MS 508 (M+H).

Example 45

1-(2,4-Difluoro-phenyl)-6-fluoro-4-oxo-7-(3-pyridin-3-yl-3a,4,6,6a-tetrahydro-pyrrolo[3,4-d]isoxazol-5-yl)-1,4-dihydro-[1,8]naphthyridine-3-carboxylic acid (105)

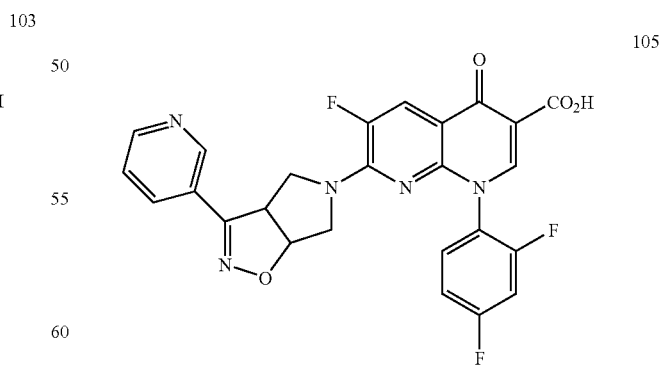

The title compound was prepared in an analogous manner to acid 101, but using a suitably substituted TFA salt 4f. Acid 105 was isolated as a beige solid.
MS 508 (M+H).

Example 46

1-(2,4-Difluoro-phenyl)-7-(3-ethoxycarbonyl-3a,4,6,6a-tetrahydro-pyrrolo[3,4-d]isoxazol-5-yl)-6-fluoro-4-oxo-1,4-dihydro-[1,8]naphthyridine-3-carboxylic acid (106)

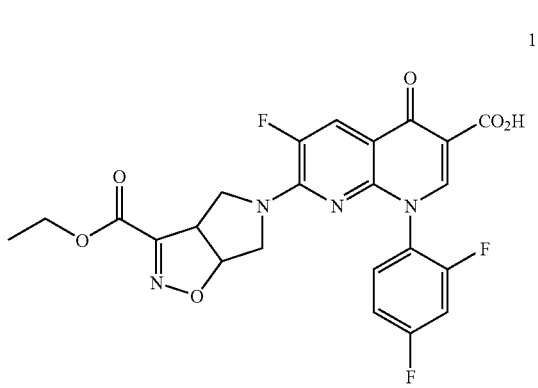

106

The title compound was prepared in an analogous manner to acid 101, but using a suitably substituted TFA salt 10. Acid 106 was isolated as a brown solid.

MS 503 (M+H).

Example 47

1-(2,4-Difluoro-phenyl)-6-fluoro-7-(3-hydroxymethyl-3a,4,6,6a-tetrahydro-pyrrolo[3,4-d]isoxazol-5-yl)-4-oxo-1,4-dihydro-[1,8]naphthyridine-3-carboxylic acid (107)

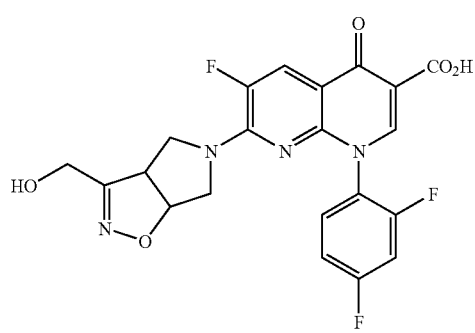

107

The title compound was prepared in an analogous manner to acid 101, but using a suitably substituted TFA salt 11. Acid 107 was isolated as a beige solid.

MS 461 (M+H).

Example 48

1-(2,4-Difluoro-phenyl)-7-[3-(1,3-dioxo-1,3-dihydro-isoindol-2-ylmethyl)-3a,4,6,6a-tetrahydro-pyrrolo[3,4-d]isoxazol-5-yl]-6-fluoro-4-oxo-1,4-dihydro-[1,8]naphthyridine-3-carboxylic acid (108)

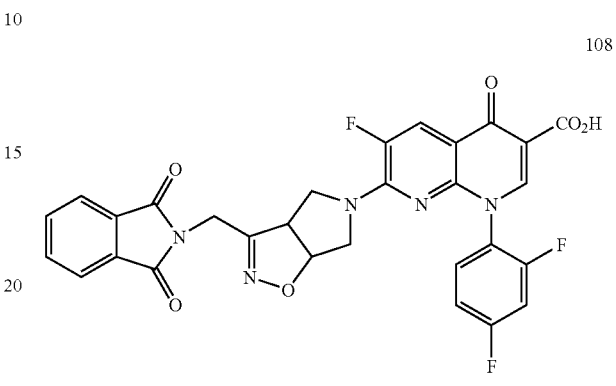

108

The title compound was prepared in analogous manner to 101 but using a suitably substituted TFA salt 9. Phthalimide 108 was isolated as a white powder.

MS 590 (M+H).

Example 49

1-Cyclopropyl-7-(2,5-dihydro-pyrrol-1-yl)-6-fluoro-4-oxo-1,4-dihydro-[1,8]naphthyridine-3-carboxylic acid (109)

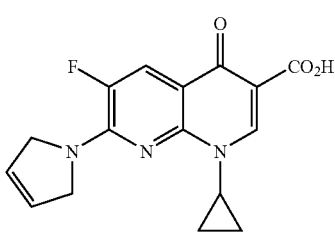

109

3-Pyrroline (1.0 g; 14.5 mmol) and acid 51 (2.0 g; 7.1 mmol) in acetonitrile (50 mL) were heated at reflux temperature overnight. The volatiles were evaporated and water added to the residue. The resulting solid was filtered, washed with water and ether to yield 109 as a beige solid.

MS 316 (M+H).

Example 50

7-[3-(4-Chloro-phenyl)-3a,4,6,6a-tetrahydro-pyrrolo[3,4-d]isoxazol-5-yl]-1-cyclopropyl-6-fluoro-4-oxo-1,4-dihydro-[1,8]naphthyridine-3-carboxylic acid (110)

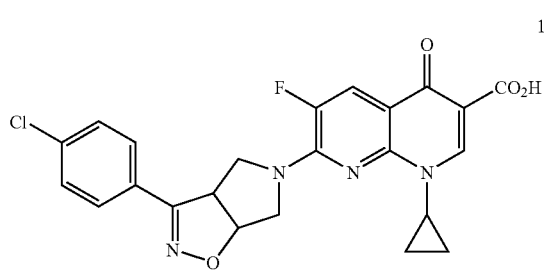

The title compound was prepared in analogous manner as acid 101, but using 7-chloro-1-cyclopropyl-6-fluoro-4-oxo-1,4-dihydronapthyridne-3-carboxylic acid (51). Acid 110 was isolated as an off-white solid.

MS 469 (M+H).

Example 51

1-Cyclopropyl-6-fluoro-7-[3-(6-methoxypyridin-3-yl)-3a,4,6,6a-tetrahydro-pyrrolo[3,4-d]isoxazol-5-yl]-4-oxo-1,4-dihydro-[1,8]naphthyridine-3-carboxylic acid (111)

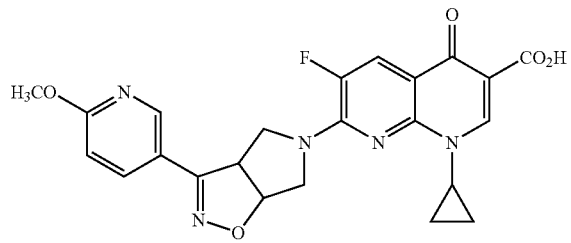

The title compound was prepared in analogous manner as acid 110. Acid 111 was isolated as a beige powder.

MS 466 (M+H).

Example 52

1-Cyclopropyl-6-fluoro-4-oxo-7-[3-(6-trifluoromethyl-pyridin-3-yl)-3a,4,6,6a-tetrahydro-pyrrolo[3,4-d]isoxazol-5-yl]-1,4-dihydro-[1,8]naphthyridine-3-carboxylic acid (112)

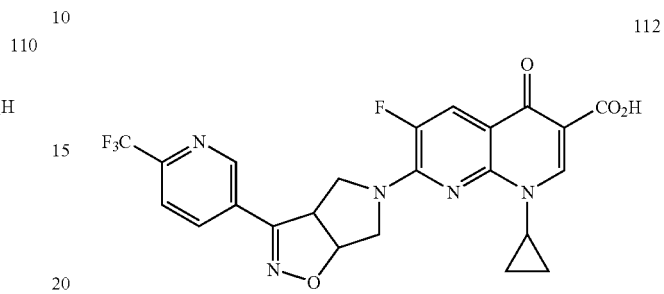

The title compound was prepared in analogous manner as acid 110. Acid 112 was isolated as a white solid.

MS 504 (M+H).

Example 53

1-Cyclopropyl-6-fluoro-4-oxo-7-(3-pyridin-2-yl-3a,4,6,6a-tetrahydro-pyrrolo[3,4-d]isoxazol-5-yl)-1,4-dihydro-[1,8]naphthyridine-3-carboxylic acid (113)

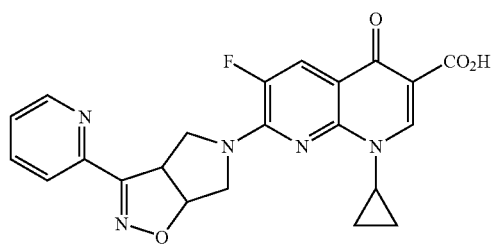

The title compound was prepared in analogous manner as acid 110. 113 was isolated.

MS 436 (M+H).

Example 54

1-Cyclopropyl-6-fluoro-4-oxo-7-(3-pyridin-3-yl-3a, 4,6,6a-tetrahydro-pyrrolo[3,4-d]isoxazol-5-yl)-1,4-dihydro-[1,8]naphthyridine-3-carboxylic acid (114)

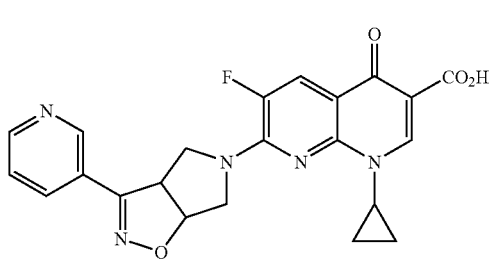

The title compound was prepared in analogous manner as acid 110. Acid 114 was isolated as a tan solid.

MS 436 (M+H).

Example 55

1-Cyclopropyl-6-fluoro-4-oxo-7-(3-pyridin-4-yl)-3a, 4,6,6a-tetrahydro-pyrrolo[3,4-d]isoxazol-5-yl)-1,4-dihydro-[1,8]naphthyridine-3-carboxylic acid (115)

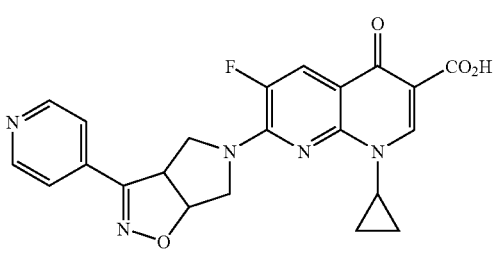

Chloro oxime 2g (156 mg; 1 mmol), olefin 109 (172 mg; 0.5 mmol) and sodium bicarbonate (100 mg) in isopropanol (10 mL) were heated at 60° C. overnight. After cooling, the reaction mixture was evaporated. The residue washed with water and then ethyl acetate. Acid 115 was isolated.

MS 436 (M+H).

Example 56

1-Cyclopropyl-7-(3-ethoxycarbonyl-3a,4,6,6a-tetrahydro-pyrrolo[3,4-d]isoxazol-5-yl)-6-fluoro-4-oxo-1,4-dihydro-[1,8]naphthyridine-3-carboxylic acid (116)

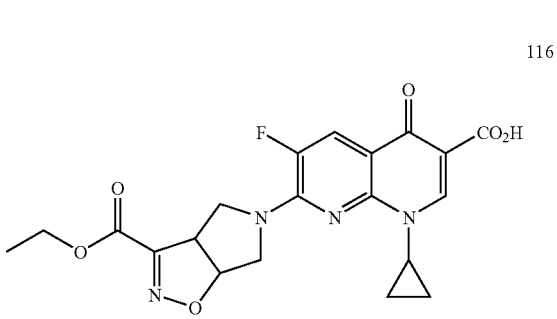

The title compound was prepared in analogous manner as acid 110.

MS 431 (M+H).

Example 57

1-Cyclopropyl-6-fluoro-7-(3-hydroxymethyl-3a,4,6, 6a-tetrahydro-pyrrolo[3,4-d]isoxazol-5-yl)-4-oxo-1, 4-dihydro-[1,8]naphthyridine-3-carboxylic acid (117)

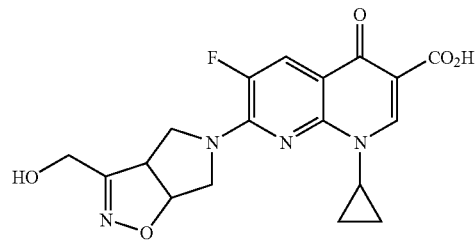

The title compound was prepared in analogous manner as acid 110. Acid 117 was isolated as a beige solid.

MS 389 (M+H).

Example 58

1-Cyclopropyl-7-[3-(1,3-dioxo-1,3-dihydro-isoindol-2-ylmethyl)-3a,4,6,6a-tetrahydro-pyrrolo[3,4-d]isoxazol-5-yl]-6-fluoro-4-oxo-1,4-dihydro-[1,8]naphthyridine-3-carboxylic acid (118)

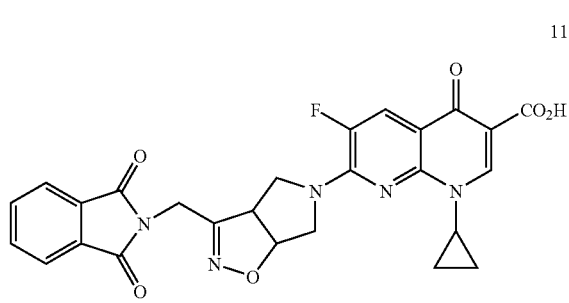

The title compound was prepared in analogous manner as acid 110. Acid 118 was isolated as a white solid.

MS 518 (M+H).

Example 59

1-Cyclopropyl-7-(2,5-dihydro-pyrrol-1-yl)-6-fluoro-8-methoxy-4-oxo-1,4-dihydro-quinoline-3-carboxylic acid (119)

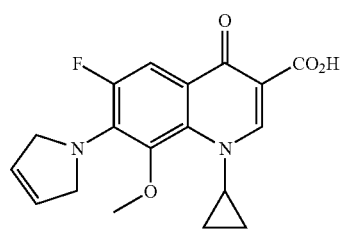

3-Pyrroline (1 g; 14.5 mmol) and acid 52 (2.1 g; 7.2 mmol) in DMF (10 mL) were heated at 100° C. overnight. After cooling, the reaction mixture was filtered and washed with water. Acid 119 was isolated.

MS 345 (M+H).

Example 60

7-[cis-3-(4-Methoxyphenyl)-3a,4,6,6a-tetrahydropyrrolo[3,4-d]isoxazol-5-yl]-1-cyclopropyl-8-methoxy-6-fluoro-4-oxo-1,4-dihydroquinoline-3-carboxylic acid (120)

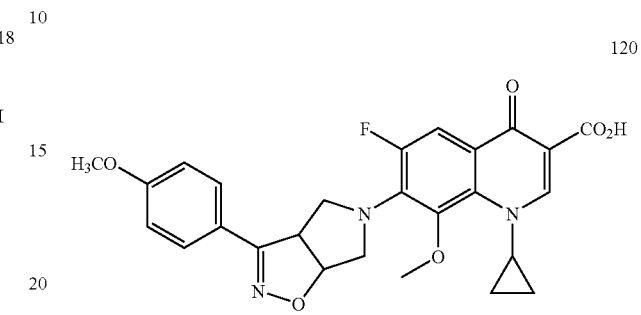

Activated core 61 (69 mg; 0.2 mmol), TFA salt 4b (71 mg; 0.22 mol) and triethylamine (0.15 ml) in DMSO (1 mL) were heated at 55° C. overnight. Ethanol (5 mL) and additional triethylamine (0.15 ml) were added and the reaction mixture heated at 78° C. for 4 hours. The volatiles were evaporated and the residue added to water. The solid was collected. The crude material was purified by reverse phase HPLC (acetonitrile/water with TFA modifier). 120 was isolated as an amber oil.

MS 494 (M+H).

Example 61

7-[cis-3-(6-Trifluoromethyl-3-pyridyl)-3a,4,6,6a-tetrahydropyrrolo[3,4-d]isoxazol-5-yl]-1-cyclopropyl-8-methoxy-6-fluoro-4-oxo-1,4-dihydroquinoline-3-carboxylic acid (121)

The title compound was prepared in an analogous manner as acid 120. Compound 121 was isolated by trituration with diethyl ether as a brown solid.

MS 533 (M+H).

Example 62

7-[cis-3-(2-pyridyl)-3a,4,6,6a-tetrahydropyrrolo[3,4-d]isoxazol-5-yl]-1-cyclopropyl-8-methoxy-6-fluoro-4-oxo-1,4-dihydroquinoline-3-carboxylic acid (122)

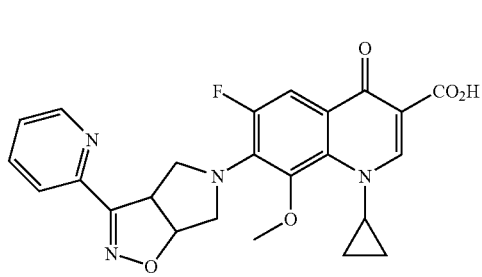

122

Chloro oxime 2e (70 mg; 0.44 mmol), olefin 119 (100 mg; 0.29 mmol) and sodium bicarbonate (50 mg) in ethyl acetate (10 mL) were heated at reflux temperature overnight. The solid was filtered and the filtrate evaporated. The residue was triturated with methanol to yield acid 122.

MS 465 (M+H).

Example 63

7-[cis-3-(3-Pyridyl)-3a,4,6,6a-tetrahydropyrrolo[3,4-d]isoxazol-5-yl]-1-cyclopropyl-8-methoxy-6-fluoro-4-oxo-1,4-dihydroquinoline-3-carboxylic acid (123)

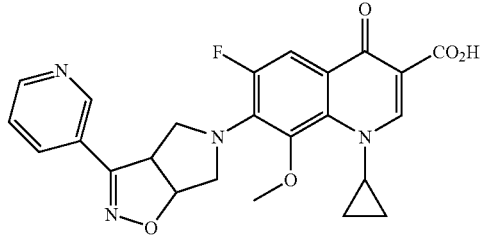

123

The title compound was prepared in an analogous manner to acid 122, but using chloro oxime 2f. Acid 123 was isolated.

MS 465 (M+H).

Example 64

7-[cis-3-(3-Ethoxycarbonyl)-3a,4,6,6a-tetrahydropyrrolo[3,4-d]isoxazol-5-yl]-1-cyclopropyl-8-methoxy-6-fluoro-4-oxo-1,4-dihydroquinoline-3-carboxylic acid (124)

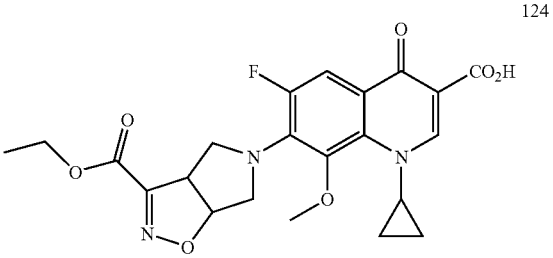

124

The title compound was prepared in an analogous manner as acid 120 but using acetonitrile as the solvent instead of DMSO. Acid 124 was isolated as a beige powder.

MS 460 (M+H).

Example 65

7-[3-(1,3-dioxo-1,3-dihydro-isoindol-2-ylmethyl)-3a,4,6,6a-tetrahydro-pyrrolo[3,4-d]isoxazol-5-yl]-1-cyclopropyl-8-methoxy-6-fluoro-4-oxo-1,4-dihydro-quinoline-3-carboxylic acid (125)

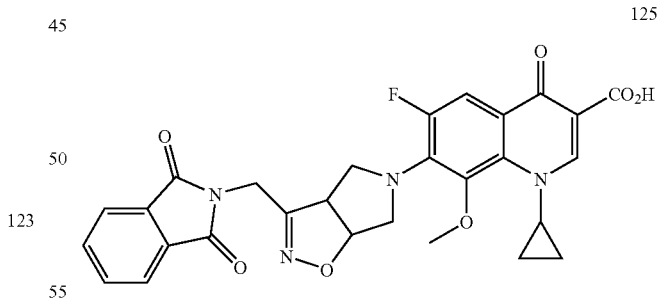

125

Difluoroborate ester 61 (70 mg, 0.204 mmol), TFA salt 9 (86 mg; 0.223 mmol) and triethylamine (0.15 mL) in DMSO (1 mL) were heated at 55° C. under a nitrogen atmosphere overnight. Ethanol (5 mL) was added followed by additional triethylamine (0.15 mL). The reaction mixture was stirred at 80° C. for 4 hours. The volatiles were evaporated and water was added to the residue. The resulting solid was collected, washed with water, methanol and dried. 125 was isolated as a light beige powder.

MS 547 (M+H).

Example 66

7-[cis-3-(4-Methoxyphenyl)-3a,4,6,6a-tetrahydropyr-rolo[3,4-d]isoxazol-5-yl]-1-[(1R,2S)-2-fluorocyclo-propyl]-6-fluoro-8-methoxy-4-oxo-1,4-dihydro-quinoline-3-carboxylic acid (126)

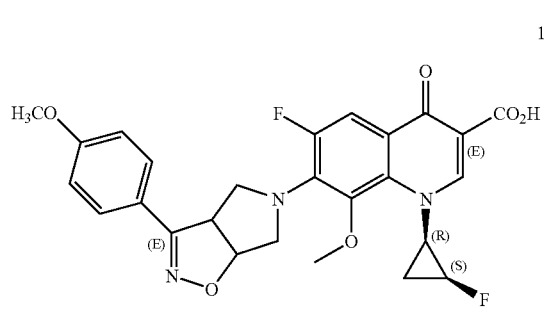

Activated core 60 (73 mg; 0.2 mmol), TFA salt 4b (71 mg; 0.22 mmol) and triethylamine (0.15 mL) in DMSO (1 mL) were heated at 55° C. overnight. Ethanol (5 mL) and an additional amount of triethylamine (0.15 mL) were added and the reaction mixture heated at 78° C. for 4 hours. After cooling, the volatiles were evaporated and the residue added to water. The resulting solid was isolated by filtration. Purification by reverse phase HPLC (acetonitrile/water with no TFA modifier) yielded 126 as a yellow-brown powder.

MS 512(M+H).

Example 68

7-[cis-3-(4-Methoxyphenyl)-3a,4,6,6a-tetrahydropyr-rolo[3,4-d]isoxazol-5-yl]S-(−)-9,10-difluoro-2,3-dihydro-3-methyl-7-oxo-7H-pyrido-[1,2,3-de][1,4]-benzoxazine-6-carboxylic acid (128)

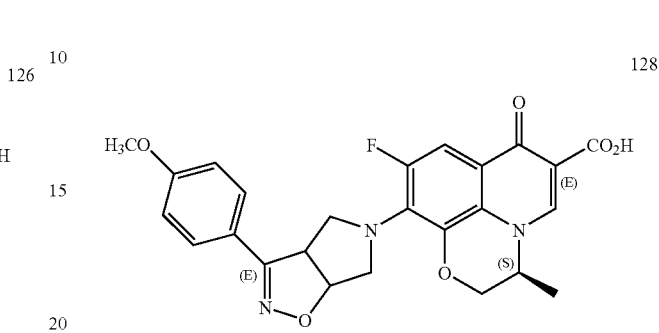

Activated core 58 (66 mg; 0.2 mmol), TFA salt 4b (71 mg; 0.22 mmol) and triethylamine (0.15 mL) in DMSO (1 mL) were heated at 55° C. overnight. Ethanol (5 mL) and an additional amount of triethylamine (0.15 mL) were added and the reaction mixture heated at 78° C. for 4 hours. After cooling, the volatiles were evaporated and the residue added to water. The resulting solid was collected, washed with water and dried. Purification by reverse phase HPLC (acetonitrile/water with no TFA modifier) yielded product 128 as a yellow powder.

MS 480 (M+H).

Example 67

7-[3-(1,3-dioxo-1,3-dihydro-isoindol-2-ylmethyl)-3a,4,6,6a-tetrahydro-pyrrolo[3,4-d]isoxazol-5-yl]-1-[(1R,2S)-2-fluorocyclopropyl]-6-fluoro-8-methoxy-4-oxo-1,4-dihydro-quinoline-3-carboxylic acid (127)

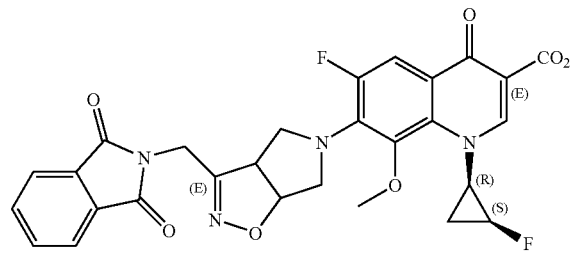

The title compound was prepared as above for 126 using a suitably substituted TFA salt 9. 127 was isolated as a beige powder.

MS 565 (M+H).

Example 69

7-[cis-3-(2-pyridyl)-3a,4,6,6a-tetrahydropyrrolo[3,4-d]isoxazol-5-yl]S-(−)-9,10-difluoro-2,3-dihydro-3-methyl-7-oxo-7H-pyrido-[1,2,3-de][1,4]-benzoxazine-6-carboxylic acid (129)

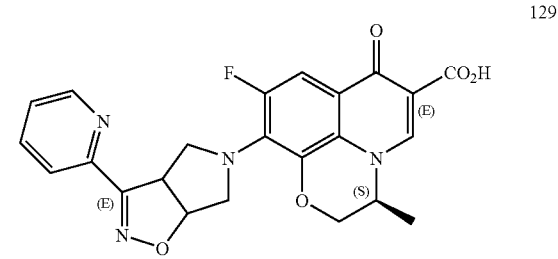

The title compound was prepared in an analogous manner to acid 128 but using TFA salt 4e. Acid 129 was isolated.

MS 452 (M+H).

Example 70

7-[cis-3-(3-pyridyl)-3a,4,6,6a-tetrahydropyrrolo[3,4-d]isoxazol-5-yl]S-(−)-9,10-difluoro-2,3-dihydro-3-methyl-7-oxo-7H-pyrido-[1,2,3-de][1,4]-benzoxazine-6-carboxylic acid (130)

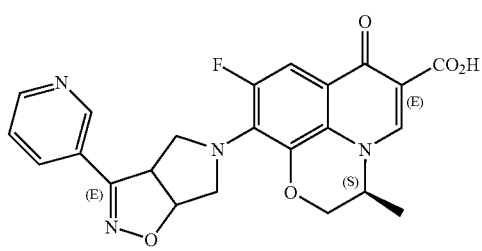

The title compound was prepared in analogous manner to acid 128, but using TFA salt 4f. Acid 130 was isolated by reverse phase HPLC (acetonitrile/water and no trifluoroacetic acid modifier) as a pale yellow powder.

MS 451 (M+H).

Example 71

7-[cis-3-(ethoxycarbonyl)-3a,4,6,6a-tetrahydropyrrolo[3,4-d]isoxazol-5-yl]S-(−)-9,10-difluoro-2,3-dihydro-3-methyl-7-oxo-7H-pyrido-[1,2,3-de][1,4]-benzoxazine-6-carboxylic acid (131)

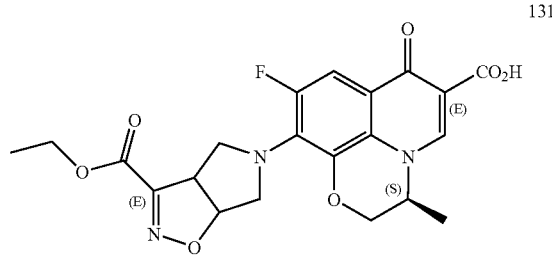

The title compound was prepared in an analogous manner to acid 128, but using TFA salt 10. Acid 131 was isolated.

MS 446 (M+H).

Example 72

7-[3-(1,3-dioxo-1,3-dihydro-isoindol-2-ylmethyl)-3a,4,6,6a-tetrahydro-pyrrolo[3,4-d]isoxazol-5-yl]-S-(−)-9,10-difluoro-2,3-dihydro-3-methyl-7-oxo-7H-pyrido-[1,2,3-de][1,4]-benzoxazine-6-carboxylic acid (132)

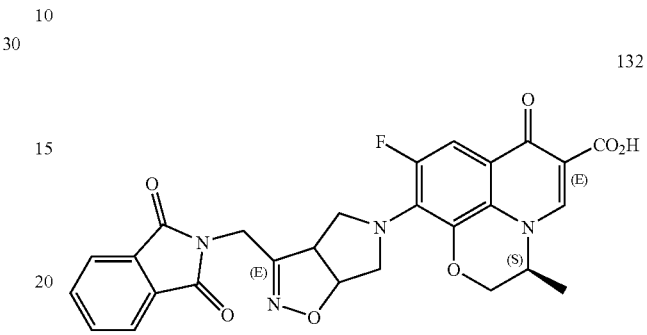

The title compound was prepared as above for 128 using a suitably substituted TFA salt 9. 132 was isolated as a yellow powder.

MS 533 (M+H).

Example 73

1-(6-Amino-3,5-difluoro-pyridin-2-yl)-8-chloro-6-fluoro-7-[3-(4-methoxy-phenyl)-3a,4,6,6a-tetrahydro-pyrrolo[3,4-d]isoxazol-5-yl]-4-oxo-1,4-dihydro-quinoline-3-carboxylic acid (133)

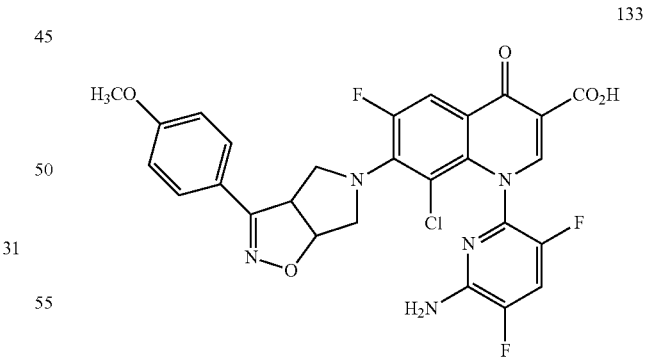

Acid 55 (78 mg; 0.2 mmol), TFA salt 4b (71 mg; 0.22 mmol) and triethylamine (0.15 mL) in DMSO (1 mL) were heated at 55° C. for 2 days. The reaction mixture was concentrated and the residue was triturated with water. The solid was chromatographed by reverse phase HPLC (acetonitrile/water with no TFA modifier) to yield 133 as a yellow brown powder.

MS 587 (M+H).

Example 74

1-Cyclopropyl-6-fluoro-7-[3-(6-methoxy-pyridin-3-yl)-3a,4,6,6a-tetrahydro-pyrrolo[3,4-d]isoxazol-5-yl]-4-oxo-1,4-dihydro-quinoline-3-carboxylic acid (134)

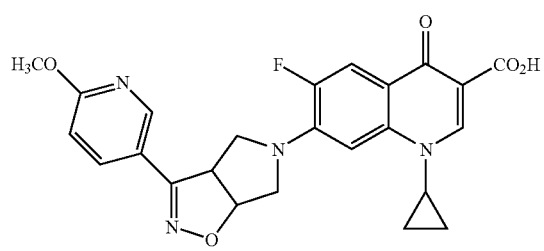

Acid 56 (93 mg; 0.35 mmol), TFA salt 4c (231 mg; 0.52 mmol) and triethylamine (0.4 mL) in acetonitrile (5 mL) were heated at reflux temperature for 2 days. The volatiles were evaporated and water added to the residue. The resulting solid was collected, washed with water and dried. The resulting residue was purified by conversion to the hydrochloride salt by the addition of HCl in ether to a solution of crude 134 in acetonitrile. The hydrochloride salt 134 was isolated as a yellow solid.

MS 465 (M+H).

Example 75

1-Cyclopropyl-6-fluoro-7-[3-(pyridin-2-yl)-3a,4,6,6a-tetrahydro-pyrrolo[3,4-d]isoxazol-5-yl]-4-oxo-1,4-dihydro-quinoline-3-carboxylic acid (135)

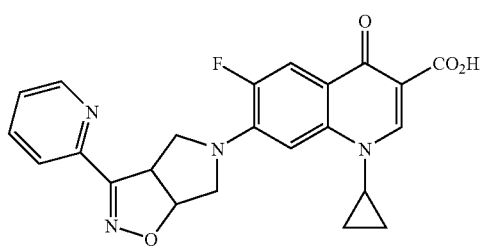

Acid 56 (66 mg; 0.25 mmol), TFA salt 4e (220 mg; 0.52 mmol) and triethylamine (0.4 mL) in DMSO (1.5 mL) were heated at 130° C. for 1.5 hours. The DMSO was distilled off. Methanol was added to the remaining oil. The resulting solid was collected and dried to yield 135. MS 435 (M+H).

Example 76

1-Cyclopropyl-6-fluoro-7-[3-(pyridin-3-yl)-3a,4,6,6a-tetrahydro-pyrrolo[3,4-d]isoxazol-5-yl]-4-oxo-1,4-dihydro-quinoline-3-carboxylic acid (136)

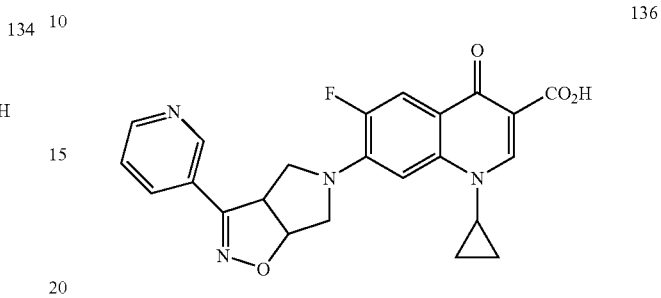

The title compound was prepared in an analogous manner as for 135, but using the TFA salt 4f. Acid 136 was isolated. MS435(M+H).

Example 77

1-Cyclopropyl-8-difluoromethoxy-7-[3-(1,3-dioxo-1,3-dihydro-isoindol-2-ylmethyl)-3a,4,6,6a-tetrahydro-pyrrolo[3,4-d]isoxazol-5-yl]-6-fluoro-4-oxo-1,4-dihydro-quinoline-3-carboxylic acid (137)

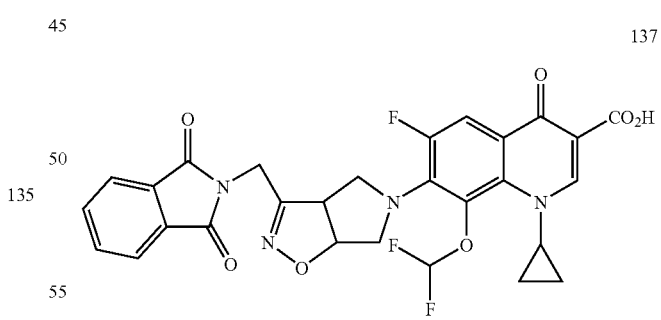

Activated core 59 (0.25 mmol), TFA salt 9 (116 mg; 0.30 mmol) and triethyl amine (0.5 mL) in acetonitrile (5 mL) were heated at reflux temperature overnight. Ethanol (5 mL) and triethylamine (0.5 mL) were added and the reaction mixture heated for 4.5 hours. After cooling, the volatiles were evaporated. Water was added and the resulting precipitate filtered. The solid was washed with chloroform and the organic filtrate evaporated to yield acid 137 as a yellow solid.

MS 583 (M+H).

Example 78

7-[cis-3-(2-pyridyl)-3a,4,6,6a-tetrahydropyrrolo[3,4-d]isoxazol-5-yl]-1-cyclopropyl-8-methoxy-4-oxo-1,4-dihydroquinoline-3-carboxylic acid (150)

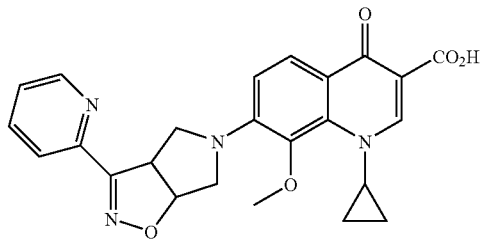

The title compound was prepared according to the procedure for the synthesis of 120, but using activated core 71 and TFA salt 4e. Acid 150 was isolated in 23% yield.

MS 447 (M+H).

Removal of Phthalimide Protecting Group

Examples 79-83 describe preparation of representative compounds of formula (I) wherein the phthalimide protecting group is removed.

Example 79

7-(3-Aminomethyl-3a,4,6,6a-tetrahydro-pyrrolo[3,4-d]isoxazol-5-yl)-1-(2,4-difluoro-phenyl)-6-fluoro-4-oxo-1,4-dihydro-[1,8]naphthyridine-3-carboxylic acid (200)

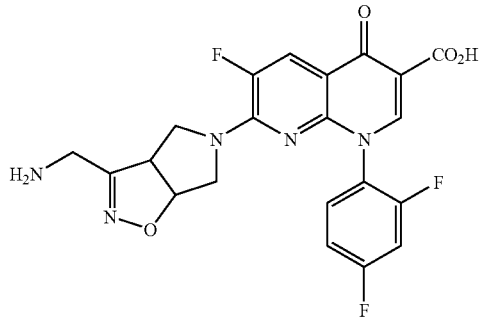

Phthalimide 108 (241 mg; 0.409 mmol) and hydrazine hydrate (0.03 mL) in ethanol (5 mL) were heated at reflux temperature under a nitrogen atmosphere for 23 hours. After cooling, the thick reaction mixture suspension was filtered. The solid was washed with methylene chloride, water and dried to yield amine 200 as an off-white solid.

MS 460 (M+H).

Example 80

7-(3-Aminomethyl-3a,4,6,6a-tetrahydro-pyrrolo[3,4-d]isoxazol-5-yl)-1-cyclopropyl-6-fluoro-4-oxo-1,4-dihydro-[1,8]naphthyridine-3-carboxylic acid (201)

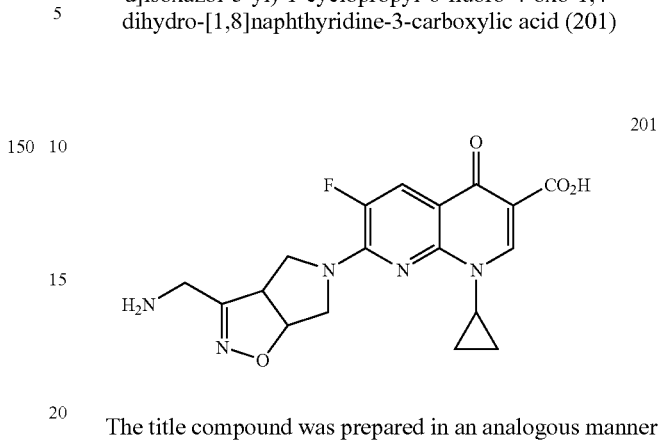

The title compound was prepared in an analogous manner as for 200, but using phthalimide 118. Amine 201 was isolated as an off-white solid.

MS 388 (M+H).

Example 81

7-[3-Aminomethyl)-3a,4,6,6a-tetrahydro-pyrrolo[3,4-d]isoxazol-5-yl]-1-cyclopropyl-8-methoxy-6-fluoro-4-oxo-1,4-dihydroquinoline-3-carboxylic acid (202)

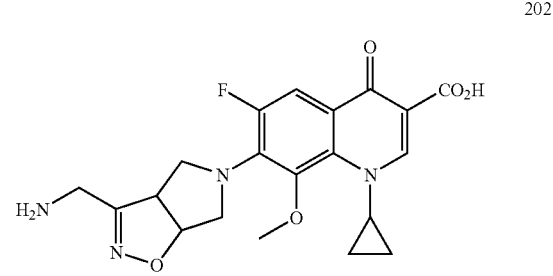

Phthalimide 125 (60 mg, 0.11 mmol) and hydrazine (0.03 mL) in methanol (5 mL) were heated at reflux temperature for 4 hours. The resulting mixture was concentrated and water added to the residue. No solid formed. The water was evaporated and the residue was purified by reverse phase HPLC (acetonitrile/water with no TFA modifier). 202 was isolated as a yellow powder.

MS 417 (M+H).

Example 82

7-[3-Aminomethyl]-3a,4,6,6a-tetrahydro-pyrrolo[3,4-d]isoxazol-5-yl]-1-[(1R,2S)-2-fluorocyclopropyl]-6-fluoro-8-methoxy-4-oxo-1,4-dihydro-quinoline-3-carboxylic acid (203)

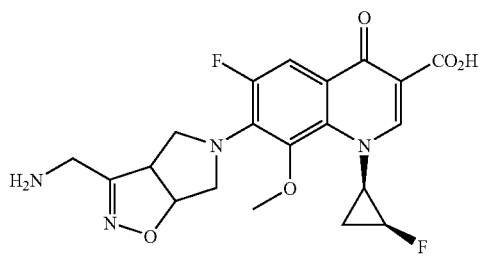

The title compound was prepared by an analogous procedure as for 202. The crude material was purified by reverse phase HPLC (acetonitrile/water with no TFA modifier). 203 was isolated as a yellow powder.
MS 435 (M+H).

Example 83

7-[3-Aminomethyl]-3a,4,6,6a-tetrahydro-pyrrolo[3,4-d]isoxazol-5-yl]-S-(−)-9,10-difluoro-2,3-dihydro-3-methyl-7-oxo-7H-pyrido-[1,2,3-de][1,4]-benzoxazine-6-carboxylic acid (204)

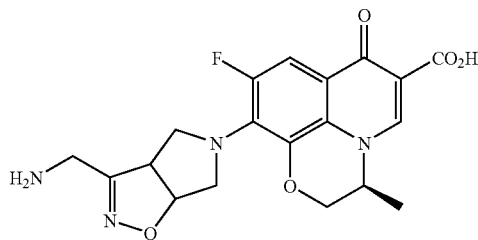

The title compound was prepared by an analogous procedure as for 202. Purification was done by reverse phase HPLC (acetonitrile/water with no TFA modifier). 204 was isolated as a yellow powder.
MS 403 (M+H).

Example 84

Biological Activity

The compounds described in the present invention possess antibacterial activity due to their novel structure, and are useful as antibacterial agents for the treatment of bacterial infections in humans and animals.

Minimal inhibitory concentration (MIC) has been an indicator of in vitro antibacterial activity widely used in the art. The in vitro antimicrobial activity of representative compounds of the present invention was determined by the microdilution broth method following the test method from the National Committee for Clinical Laboratory Standards (NCCLS). This method is described in the NCCLS Document M7-A4, Vol. 17, No. 2, "Methods for Dilution Antimicrobial Susceptibility Test for Bacteria that Grow Aerobically—Fourth Edition", which is incorporated herein by reference.

In this method two-fold serial dilutions of drug in cation adjusted Mueller-Hinton broth are added to wells in microdilution trays. The test organisms are prepared by adjusting the turbidity of actively growing broth cultures so that the final concentration of test organism after it is added to the wells is approximately $5 \times 10^4$ CFU/well.

Following inoculation of the microdilution trays, the trays are incubated at 35° C. for 16-20 hours and then read. The MIC is the lowest concentration of test compound that completely inhibits growth of the test organism. The amount of growth in the wells containing the test compound is compared with the amount of growth in the growth-control wells (no test compound) used in each tray. As set forth in Table 4, representative compounds of the present invention were tested against a variety of pathogenic bacteria resulting in a range of activities depending on the organism tested.

TABLE 4

| ID No. | A | B | C | D | E |
|---|---|---|---|---|---|
| 101 | 0.06 | 1 | 2 | 4 | 1 |
| 102 | 0.06 | 4 | 16 | 2 | 1 |
| 103 | 0.25 | 8 | >16 | 4 | 2 |
| 104 | 0.06 | 0.5 | 2 | 4 | 1 |
| 105 | 0.06 | 0.5 | 2 | 2 | 1 |
| 106 | 0.12 | >16 | >16 | >16 | 8 |
| 107 | 0.12 | >16 | >16 | >16 | 2 |
| 108 | 0.25 | >16 | >16 | >16 | 8 |
| 200 | 0.12 | >16 | >16 | >16 | 1 |
| 110 | 0.06 | ND | 8 | ND | 0.5 |
| 111 | 0.03 | 8 | 4 | 2 | 0.5 |
| 112 | 0.25 | 16 | >16 | 8 | 2 |
| 113 | 0.06 | 16 | 2 | 4 | 1 |
| 114 | 0.12 | ND | 2 | 8 | 1 |
| 115 | 0.06 | 16 | 8 | 4 | 1 |
| 116 | 0.12 | >16 | >16 | >16 | 4 |
| 117 | 0.5 | 16 | 16 | 16 | 8 |
| 118 | 2 | >16 | >16 | >16 | 16 |
| 201 | 0.5 | >16 | >16 | >16 | 4 |
| 120 | 0.06 | ND | 4 | 2 | 1 |
| 121 | 0.25 | .16 | >16 | 8 | 4 |
| 122 | <0.12 | 16 | 16 | 2 | 1 |
| 123 | 0.06 | 8 | 8 | 2 | 0.5 |
| 124 | 0.25 | >16 | >16 | >16 | 8 |
| 125 | | | | | |
| 202 | 0.06 | ND | 16 | >16 | 1 |
| 126 | 0.03 | ND | 4 | 2 | 0.5 |
| 127 | | | | | |
| 203 | 0.12 | ND | >16 | >16 | 2 |
| 128 | 0.12 | ND | 4 | 4 | 1 |
| 129 | 0.06 | >16 | 16 | 4 | 1 |
| 130 | 0.25 | ND | 16 | 16 | 2 |
| 131 | 1 | >16 | >16 | >16 | 16 |
| 132 | | | | | |
| 204 | 0.25 | ND | >16 | >16 | 16 |
| 133 | 0.25 | ND | 8 | 16 | 2 |
| 134 | 0.12 | 16 | >16 | 8 | 2 |
| 135 | 0.03 | 8 | 2 | 4 | 1 |
| 136 | 0.06 | 8 | 4 | 8 | 1 |
| 137 | | | | | |
| 150 | 0.06 | >16 | 8 | 8 | 1 |

A: *Staphylococcus aureus* OC4172;
strains B, C, and D are fluoroquinolone-resistant clinical isolates of *Streptococcus pneumoniae* that contain different constellations of amino acid substitutions in the QRDR region;
E: *Streptococcus pneumoniae* ATCC 49619.
The abbreviation "ND" indicates that the value was not determined.

Example 85

Formulation Example

As a specific embodiment of an oral composition, 100 mg of compound #126 is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of formula (I)

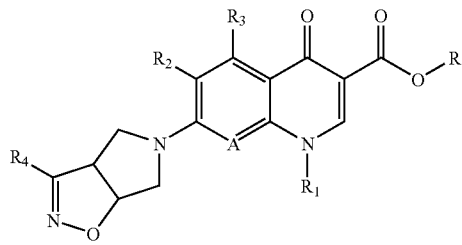

wherein

R is selected from the group consisting of hydrogen and lower alkyl;

$R_1$ is selected from the group consisting of $C_3$-$C_6$cycloalkyl, $C_4$-$C_6$heterocycloalkyl, $C_1$-$C_8$alkyl, $C_2$-$C_8$alkenyl, phenyl and a 5 to 6 membered heteroaryl;

wherein the $C_3$-$C_6$cycloalkyl, $C_4$-$C_6$heterocycloalkyl, phenyl or 5 to 6 membered heteroaryl is optionally substituted with one to four substituents independently selected from the group consisting of halogen, lower alkyl, lower alkoxy, cyano, nitro, amino, (lower alkyl)amino and di(lower alkyl)amino;

A is selected from the group consisting of $CR_5$; wherein $R_5$ is selected from the group consisting of hydrogen, halogen, hydroxyl, lower alkyl, halogenated lower alkyl, lower alkoxy, halogenated lower alkoxy, $C_1$-$C_4$alkylthio, amino, (lower alkyl)amino, di(lower alkyl)amino and cyano;

alternatively, A is $CR_5$, and $R_5$ and $R_1$ are taken together with the atoms to which they are bound to form

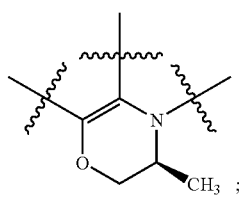

$R_2$ and $R_3$ are each independently selected from the group consisting of hydrogen, halogen, hydroxy, amino, (lower alkyl)amino, di(lower alkyl)amino, lower alkoxy, $C_1$-$C_4$alkylthio, lower alkyl, $C_2$-$C_4$alkenyl and $C_2$-$C_4$alkynyl;

$R_4$ is selected from the group consisting of $C_1$-$C_8$alkyl, —C(O)O-(lower alkyl), aryl, heteroaryl, heterocloalkyl, —($C_1$-$C_4$alkyl)-$C_3$-$C_6$cycloalkyl, —($C_1$-$C_4$alkyl)-aryl, —($C_1$-$C_4$alkyl)-heteroaryl, and —($C_{1-4}$alkyl)-heterocycloalkyl;

wherein the $C_1$-$C_8$alkyl is optionally substituted with one or more substituents independently selected from the group consisting of halogen, hydroxy, amino, (lower alkyl)amino, di(lower alkyl)amino, aryloxy, heteroaryloxy, acyloxy, carboxy, carboxamido, acylamino, oxo, thio, and cyano;

and wherein the aryl, heteroaryl or heterocycloalkyl, whether alone or as part of a substituent group, is optionally substituted with one to three substituents independently selected from the group consisting of halogen, hydroxy, oxo, cyano, mercapto, nitro, amino, (lower alkyl)amino, di(lower alkyl)amino, $C_1$-$C_8$-alkyl, halogenated $C_1$-$C_8$alkyl, $C_1$-$C_8$alkoxy, halogenated $C_1$-$C_8$alkoxy, $C_1$-$C_8$alkylthio, formyl, carboxy, —C(O)O-(lower alkyl), —O—C(O)—($C_1$-$C_8$-alkyl), —NH—C(O)—($C_1$-$C_8$-alkyl), carboxamide, a second aryl and a second heteroaryl;

and wherein the second aryl or second heteroaryl is optionally substituted with one or more substituents independently selected from the group consisting of halogen, hydroxy, cyano, nitro, amino, (lower alkyl)amino, di(lower alkyl)amino, $C_1$-$C_8$-alkyl, halogenated $C_1$-$C_8$alkyl, $C_1$-$C_8$alkoxy, halogenated $C_1$-$C_8$alkoxy, $C_1$-$C_8$alkylthio, carboxy and —C(O)O-(lower alkyl);

or optical isomer, diastereomer, enantiomer, pharmaceutically acceptable salt thereof.

2. A compound as in claim 1, wherein

R is selected from the group consisting of hydrogen, methyl, ethyl and t-butyl;

$R_1$ is selected from the group consisting of $C_{3-6}$cycloalkyl, $C_{4-6}$heterocycloalkyl, phenyl, and 6 membered heteroaryl; wherein the $C_{3-6}$cycloalkyl, $C_{4-6}$heterocycloalkyl, phenyl or 6 membered heteroaryl is optionally substituted with one to three substituents independently selected from the group consisting of halogen, lower alkyl, lower alkoxy, cyano, amino, (lower alkyl)amino and di(lower alkyl)amino;

A is selected from the group consisting of $CR_5$; wherein $R_5$ is selected from the group consisting of hydrogen, halogen, lower alkyl, fluorinated lower alkyl, lower alkoxy and fluorinated lower alkoxy;

alternatively, A is $CR_5$, and $R_5$ and $R_1$ are taken together with the atoms to which they are bound to form

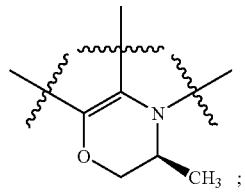

$R_2$ and $R_3$ are each independently selected from the group consisting of hydrogen, halogen, hydroxy, amino, (lower alkyl)amino, di(lower alkyl)amino, lower alkyl and lower alkoxy;

$R_4$ is selected from the group consisting of lower alkyl, —C(O)O-(lower alkyl), aryl, heteroaryl, heterocloalkyl, —($C_1$-$C_2$alkyl)-heteroaryl and —($C_1$-$C_2$alkyl)-heterocycloalkyl;

wherein the lower alkyl is optionally substituted with one to two substitutent independently selected from the group consisting of halogen, hydroxy, amino, (lower alkyl)amino, di(lower alkyl)amino, aryloxy, heteroaryloxy, acyloxy, carboxy, oxo and cyano;

wherein the aryl, heteroaryl or heterocycloalkyl, whether alone or as part of a substituent group is optionally substituted with one to two substituents independently selected from the group consisting of halogen, hydroxy, cyano, amino, (lower alkyl)amino, di(lower alkyl)amino, lower alkyl, halogenated lower alkyl, lower alkoxy, halogenated lower alkoxy, oxo, carboxy and —C(O)O-(lower alkyl);

or optical isomer, diastereomer, enantiomer, pharmaceutically acceptable salt thereof.

3. A compound as in claim 2, wherein

R is hydrogen;

$R_1$ is selected from the group consisting of $C_3$-$C_6$cycloalkyl, phenyl, and 6 membered heteroaryl; wherein the $C_3$-$C_6$cycloalkyl, phenyl or 6 membered heteroaryl is optionally substituted with one to three substituents independently selected from the group consisting of halogen and amino;

A is selected from the group consisting of $CR_5$; wherein $R_5$ is selected from the group consisting of hydrogen, halogen, lower alkoxy and fluorinated lower alkoxy;

alternatively, A is $CR_5$ and $R_5$ and $R_1$ are taken together with the atoms to which they are bound to form

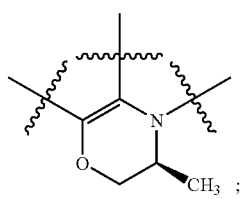

$R_2$ is halogen;

$R_3$ is hydrogen;

$R_4$ is selected from the group consisting of lower alkyl, phenyl, 6 membered heteroaryl, 2-(isoindole-1,3-dione)-methyl-, and —C(O)O-lower alkyl;

wherein the lower alkyl is optionally substituted with a substitutent selected from the group consisting of hydroxy and amino;

wherein the phenyl or 6 membered heteroaryl is optionally substituted with a substituent selected from the group consisting of halogen, lower alkoxy and fluorinated lower alkyl;

or optical isomer, diastereomer, enantiomer, pharmaceutically acceptable salt.

4. A compound as in claim 3, wherein

R is hydrogen;

$R_1$ is selected from the group consisting of cyclopropyl, 2,4-difluorophenyl 1R-(2S-fluoro-cyclopropyl) and 2-(3,5-difluoro-6-amino-pyridyl);

A is selected from the group consisting of $CR_5$; wherein $R_5$ is selected from the group consisting of hydrogen, chloro, methoxy and difluoromethoxy;

alternatively, A is $CR_5$ and $R_5$ and $R_1$ are taken together with the atoms to which they are bound to form

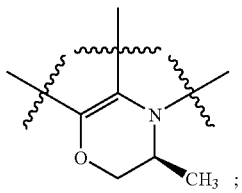

$R_2$ is fluoro;

$R_3$ is hydrogen;

$R_4$ is selected from the group consisting of ethoxy-carbonyl-, hydroxy-methyl-, amino-methyl-, 4-chlorophenyl, 4-methoxy-phenyl, 2-(isoindole-1,3-dione)-methyl-, 2-pyridyl, 3-pyridyl, 4-pyridyl, 3-(6-methoxy-pyridyl) and 3-(6-trifluoromethyl-pyridyl);

or optical isomer, diastereomer, enantiomer, pharmaceutically acceptable salt thereof.

5. A compound as in claim 4, wherein

R is hydrogen;

$R_1$ is selected from the group consisting of cyclopropyl, 2,4-difluorophenyl and 1R-(2S-fluoro-cyclopropyl);

A is selected from the group consisting of $CR_5$; wherein $R_5$ is selected from the group consisting of hydrogen and methoxy;

alternatively, A is $CR_5$ and $R_5$ and $R_1$ are taken together with the atoms to which they are bound to form

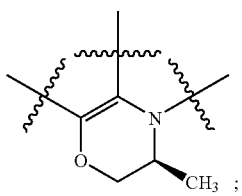

$R_2$ is fluoro;

$R_3$ is hydrogen;

$R_4$ is selected from the group consisting of 4-chlorophenyl, 4-methoxy-phenyl, 2-pyridyl, 3-pyridyl, 4-pyridyl, 3-(6-methoxy-pyridyl) and 3-(6-trifluoromethyl-pyridyl);

or optical isomer, diastereomer, enantiomer, pharmaceutically acceptable salt.

6. A compound as in claim 4, wherein

R is hydrogen;

$R_1$ is selected from the group consisting of cyclopropyl, 2,4-difluorophenyl and 1R-(2S-fluoro-cyclopropyl);

A is selected from the group consisting of $CR_5$, wherein $R_5$ is selected from the group consisting of hydrogen and methoxy;

alternatively, A is $CR_5$ and $R_5$ and $R_1$ are taken together with the atoms to which they are bound to form

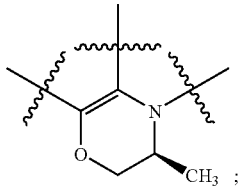

R₂ is fluoro;

R₃ is hydrogen;

R₄ is selected from the group consisting of 4-chlorophenyl, 4-methoxyphenyl, 2-pyridyl and 3-pyridyl;

or optical isomer, diastereomer, enantiomer, pharmaceutically acceptable salt thereof.

7. A compound selected from the group consisting of

1-Cyclopropyl-6-fluoro-8-methoxy-7-[3-(4-methoxy-phenyl)-3a,4,6,6a-tetrahydro-pyrrolo[3,4-d]isoxazol-5-yl]-4-oxo-1,4-dihydro-quinoline-3-carboxylic acid;

6-Fluoro-1R-(2S-fluoro-cyclopropyl)-8-methoxy-7-[3-(4-methoxy-phenyl)-3a,4,6,6a-tetrahydro-pyrrolo[3,4-d]isoxazol-5-yl]-4-oxo-1,4-dihydro-quinoline-3-carboxylic acid;

8-Fluoro-9-[3-(4-methoxy-phenyl)-3a,4,6,6a-tetrahydro-pyrrolo[3,4-d]isoxazol-5-yl]-3S-methyl-6-oxo-2,3-dihydro-6H-1-oxa-3a-aza-phenalene-5-carboxylic acid;

1-Cyclopropyl-6-fluoro-4-oxo-7-(3-pyridin-2-yl-3a,4,6,6a-tetrahydro-pyrrolo[3,4-d]isoxazol-5-yl)-1,4-dihydro-quinoline-3-carboxylic acid;

and optical isomers, diastereomers, enantiomers, pharmaceutically acceptable salts thereof.

8. A pharmaceutical composition comprising a pharmaceutically acceptable carrier and a compound of claim 1.

9. A pharmaceutical composition made by mixing a compound of claim 1 and a pharmaceutically acceptable carrier.

10. A process for making a pharmaceutical composition comprising mixing a compound of claim 1 and a pharmaceutically acceptable carrier.

* * * * *